US008620683B2

(12) United States Patent  (10) Patent No.: US 8,620,683 B2
Findlay et al.  (45) Date of Patent: Dec. 31, 2013

(54) SYSTEM AND METHOD FOR PROVIDING A MULTI-DIMENSIONAL CONTEXTUAL PLATFORM FOR MANAGING A MEDICAL PRACTICE

(75) Inventors: Nathaniel B. Findlay, Quebec (CA); Jay Parkinson, Brooklyn, NY (US); Sean Khozin, New York, NY (US); Steven Ferguson, Baie St-Paul (CA); Martin-Pierre Roy, St-Augustin (CA); Philippe Larouche, Quebec (CA); Kevin Bouchard, Quebec (CA)

(73) Assignee: Myca Health Inc., Quebec (CA)

( * ) Notice: Subject to any disclaimer, the term of this patent is extended or adjusted under 35 U.S.C. 154(b) by 0 days.

(21) Appl. No.: 13/251,934

(22) Filed: Oct. 3, 2011

(65) Prior Publication Data

US 2012/0022893 A1  Jan. 26, 2012

Related U.S. Application Data

(62) Division of application No. 12/468,563, filed on May 19, 2009.

(51) Int. Cl.
*G06Q 10/00* (2012.01)
*G06Q 50/00* (2012.01)

(52) U.S. Cl.
USPC .................................................. 705/2; 705/3

(58) Field of Classification Search
USPC ........................................................ 705/2, 3
See application file for complete search history.

(56) References Cited

U.S. PATENT DOCUMENTS

| 5,640,549 | A | 6/1997 | Powsner et al. ............... 364/578 |
| 6,757,898 | B1 | 6/2004 | Ilsen et al. .................... 718/203 |
| 2003/0125983 | A1 | 7/2003 | Flack et al. ....................... 705/2 |
| 2003/0195838 | A1 | 10/2003 | Henley ............................ 705/37 |
| 2005/0060191 | A1* | 3/2005 | Parkins et al. .................... 705/2 |
| 2005/0159986 | A1 | 7/2005 | Breeland et al. .................. 705/3 |
| 2006/0089853 | A1* | 4/2006 | Gauvin et al. .................... 705/2 |
| 2006/0265249 | A1* | 11/2006 | Follis et al. ...................... 705/3 |
| 2007/0129610 | A1 | 6/2007 | Squilla ......................... 600/300 |
| 2008/0020361 | A1 | 1/2008 | Kron et al. ..................... 434/262 |
| 2009/0083231 | A1 | 3/2009 | Eberholst et al. ................ 707/3 |
| 2009/0240522 | A1 | 9/2009 | Handal ............................. 705/2 |
| 2009/0270833 | A1 | 10/2009 | DeBelser et al. ............. 604/500 |
| 2010/0106518 | A1 | 4/2010 | Kuo ................................. 705/2 |
| 2010/0131883 | A1* | 5/2010 | Linthicum et al. ............. 715/771 |
| 2010/0217619 | A1 | 8/2010 | Cox et al. ......................... 705/2 |
| 2010/0217641 | A1 | 8/2010 | Siegel ............................... 705/8 |
| 2010/0261987 | A1 | 10/2010 | Kamath et al. ................ 600/365 |

FOREIGN PATENT DOCUMENTS

WO  WO 2009/037615  3/2009

* cited by examiner

*Primary Examiner* — Neha Patel
(74) *Attorney, Agent, or Firm* — Pillsbury Winthrop Shaw Pittman LLP

(57) ABSTRACT

A system and method is provided for generating a multi-dimensional contextual platform that may be used to manage, diagnose, and communicate with patients in a medical practice. In particular, the system may provide a website that may provide dynamic, avatar-based interfaces that include a doctor interface and a patient interface. A doctor may create a subscription with an operator of the website in order to find new patients and view patient health records across multiple dimensions. A patient may create a subscription with the operator to locate a doctor and maintain open communications with the doctor. Once subscribed, the doctor and patient may use the website to enhance the overall healthcare experience by using social networking aspects of the website to facilitate doctor and patient communication in real-time.

14 Claims, 13 Drawing Sheets

SYSTEM AND METHOD FOR PROVIDING A MULTI-DIMENSIONAL CONTEXTUAL PLATFORM FOR MANAGING A MEDICAL PRACTICE

CROSS-REFERENCE TO RELATED APPLICATION

This application is a divisional of U.S. patent application Ser. No. 12/468,563, filed May 19, 2009 (status: pending), which is hereby incorporated by reference herein in its entirety.

FIELD OF THE INVENTION

The invention relates to a system and method for providing a multi-dimensional contextual platform for managing a medical practice that uses social network tools to enhance communication between the doctor and patients.

BACKGROUND OF THE INVENTION

Increasing demands faced by medical professionals can make the process of seeking and receiving personalized healthcare a challenge for patients. From a doctor's perspective, managing a medical practice using existing systems can make treatment, organization, time management, and communication with patients difficult. For example, medical records maintained in paper files are often difficult and cumbersome to store, retrieve, and manage. Even electronic medical records may be difficult to navigate using existing systems. Since scheduling programs, health records, billing programs, and patient communication programs may span multiple platforms or applications such as calendar systems, patient database systems, and various email systems. Thus, a doctor may use unrelated systems for managing appointments, patient records, communications, and other information.

From a patient's perspective, a busy doctor often seems inattentive and communication with a doctor may be limited to office visits or short phone calls. Patients tend to feel removed from the healthcare experience because of limited interaction with their doctors as well as lack of access to their own medical information.

These and other drawbacks exist.

SUMMARY OF THE INVENTION

One aspect of the invention relates to a system and method for providing a multi-dimensional contextual platform for managing, diagnosing, and communicating with patients in a medical practice. The system may provide a website that may include dynamic, avatar-based interfaces, including a doctor interface and a patient interface. The website may also include a social networking module to facilitate doctor and patient communication in real-time, thereby enhancing the overall healthcare experience.

According to an aspect of the invention, the system may include a multi-dimensional contextual database for storing a patient's medical records and other patient information. The website may incorporate or otherwise use information from the multi-dimensional contextual database, third party health repositories, and/or other information sources.

According to an aspect of the invention, the system may include a doctor interface module for assisting the doctor in managing a medical practice. Through various modules associated with the doctor interface module, the doctor may manage the medical practice using an integrated interface that may incorporate social network tools to facilitate online and/or otherwise real-time communication between the doctor and patients. For example, the doctor interface module may include an avatar-based user interface that provides the doctor with a snapshot view of the practice, a to-do module that enables the doctor to keep track of tasks that should be performed, a prevention module that facilitates preventative healthcare maintenance of patients, a scheduling module to assist in the scheduling and reminding of appointments, an inbox module that facilitates communication, a smart grouping module for grouping patients, a search module, a cloud view module for generating a contextual display of the patient, an adaptive advising module for generating diagnostic and/or suggested courses of action, and/or other modules.

According to an aspect of the invention, the system may depict patients and doctors as avatars, thereby personalizing doctor-patient online interactions. An avatar may include a real (e.g., photo) or virtual representation of a user (e.g., doctor, patient, and/or other individual or entity interacting with the system).

In operation, a doctor may login to the website and the doctor interface module may present the avatar-based user interface. According to an aspect of the invention, the avatar-based user interface may display a number of avatars representing patients, prospective patients, colleagues, and/or other individuals or entities relevant to the doctor's practice. For example, the number of displayed avatars may represent a portion of patients or all patients in the doctor's practice, effectively providing a snapshot view of patients under the doctor's care.

To highlight recent or otherwise noteworthy information regarding patients, the avatar-based user interface may display patient events associated with patients in real-time. Patient events may include recent or otherwise noteworthy information related to the patient in which the doctor may be interested. Patient events may also be time-sensitive. As such, the avatar-based user interface may display a patient event adjacent to (or otherwise associated with) an avatar representing the patient in order to provide the doctor with real-time updates. In this manner, when interacting with the avatar-based user interface, the doctor may be notified of patient events as they occur, thereby enabling the doctor to respond to patient events in real-time.

Once logged into the website, the doctor may use various modules that facilitate management of the doctor's practice. For example, the doctor may use the to-do module to maintain and display various task items for the doctor, including, for example, items to be scheduled or performed by the doctor. A doctor or other user may enter a task item for a patient, which is displayed by the to-do module. The doctor may click or otherwise select a to-do item in order to view, change, delete, and/or perform other actions on the task item.

According to an aspect of the invention, the doctor may use the prevention module to manage preventative care of patients. The prevention module may display information related to preventative care for a patient such as, among other things, vaccinations, annual tests, and/or other preventative healthcare information. As each preventative healthcare item is performed, the doctor or other user may indicate that the item has been fulfilled, thereby helping the doctor monitor preventative healthcare for the patient.

According to an aspect of the invention, the doctor may use the scheduling module to schedule and display the doctor's appointments. Appointments may be real (e.g., in-person) or virtual (e.g., over the phone, via video-conference, web-chat, etc.). In one implementation, an appointment may be visually depicted for easy identification. For example, a scheduled phone call appointment with a patient may be represented by a telephone icon, while an in-person house call visit with a patient may be represented by a house icon. In this manner, the scheduling module may be used by the doctor to efficiently schedule and time-manage appointments.

To facilitate enhanced communications, the doctor may use the inbox module to display and respond to patient communications in real-time. Patient communications may include, among other things, general communications from patients, updates from patients, consultations from other doctors, and notifications regarding the availability of information.

General communications from patients may include any email, chat, SMS, voice, video, and/or other communications from a patient.

Updates may include particular messages from patients regarding progress related to the patient (e.g., efficacy of medications, whether the patient is feeling better, etc.).

Consultations may include messages from a specialist who may have been consulted to give their opinion of the patient. For example, the specialist may have reviewed the medical record of a patient and/or examined the patient in order to provide an opinion for the doctor to consider.

Notifications may include communications informing the doctor of the availability of information such as, among other things, lab results from a laboratory and medical records from another doctor. For example, a doctor may receive a notification that lab results for a patient are available. According to an aspect of the invention, upon reviewing the lab results, the doctor may approve releasing the lab results for review by the patient, which may cause the system to notify the patient that the lab results are available for review. By providing an integrated interface to various patient communications related to the patient's medical treatment, the inbox module may provide the doctor with the ability to make informed decisions based on information as it becomes available in real-time.

According to an aspect of the invention, the doctor may use the smart grouping module to generate and maintain patient groups. A patient group may be generated manually by the doctor, automatically by the smart grouping module according to a dimension, and/or automatically by the smart grouping module according to a common characteristic shared among patients in the patient group (such as patients taking the same medication or having the same medical condition). In this manner, the doctor may identify and manage patients according to a shared characteristic among a group of patients.

According various aspects of the invention, a doctor may identify or otherwise select a patient group to be managed. Once a patient group has been identified or otherwise selected, the doctor may perform subsequent actions for the selected group. Subsequent actions may, for example, include sending a group message, sending the group literature on a health topic, and/or any performing other actions suitable for a group. In this manner, the smart grouping module be used to perform actions on a group that would otherwise be redundantly performed for each patient in the group.

To identify patients, patient information, or search for other information associated with the system, the doctor may use the search module to search for patients by patient group, by dimension, or individually. The search module may autocomplete search terms (such as letters, words, numbers, etc.) as the search terms are being received. According to an aspect of the invention, the avatar-based user interface may integrate search results such that patients identified by search results may be dynamically highlighted in the display. Highlighting may include focusing avatars of patients in the search results to the foreground while fading other avatars to the background. Alternatively or additionally, highlighting may include enlarging, coloring differently, or otherwise altering the appearance of avatars of patients in a search results display.

According to an aspect of the invention, a highlighted avatar or group of avatars in a set of displayed search results may be selected for further processing. In other words, further processing may be performed on an individual avatar or group of avatars after the individual avatar or group of avatars have been identified by the search module. For example, clicking on (or otherwise selecting) a patient group that was identified by the search module may result in a group action to be performed as discussed above. Clicking (or otherwise selecting) an avatar may result in a patient preview display. The patient preview display may show a preview of the patient's medical record. The doctor may configure the information that is displayed in the patient preview.

Upon viewing a patient preview or otherwise selecting a particular patient to view, the doctor may use the cloud view module to interact with a multi-dimensional contextual display of the patient's health records. The cloud view module may display one or more focal points of interest for a patient, around which information related to the focal point may be arranged. Depending on the focal point and the context in which the focal point is displayed, information that may be displayed around the focal point may vary. Thus, the cloud view module may provide various views of information related to a patient's health while highlighting important aspects of the patient's health record.

According to an aspect of the invention, the doctor interface module may include an adaptive advising module for adaptively analyzing the medical record of a patient in order to advise the doctor of potential diagnoses, prognoses, and/or suggested courses of action for the patient. The adaptive advising module may continuously integrate diagnostic information in order to generate diagnoses and/or suggested courses of action. The diagnostic information may include, among other things, clinical history, prior doctor examinations of the patient, medications, test results, and prior patient outcomes. The diagnostic information may originate from the patient's health record and/or third party health repositories that include information from various patients. The adaptive advising module may adapt suggestions based on input from the doctor refining the suggestions, and/or based on information that has been added since a suggestion was made (such as a new test result or efficacy of a suggested drug). In other words, as the treatment of the patient progresses, the adaptive advising module may adaptively make suggestions based on new information. In this manner, the adaptive advising module may be used to, among other things, help the doctor diagnose, generate prognoses, and/or treat the patient.

According to an aspect of the invention, the system may include a patient interface module that may enhance the overall healthcare experience for the patient. Through various modules associated with the patient interface module, the patient may become more involved with the healthcare experience. For example, the patient interface module may include a health record module that provides access to the patient's health records and other information, an appointment module that helps the patient schedule and keep appointments with the doctor (and/or specialists), a billing module that displays the account and billing information for the patient, a notifications module for notifying the patient of recent or otherwise noteworthy information, an experts module for helping the patient track the patient's team of doctors associated with the patient, and/or other modules.

According to an aspect of the invention, the patient may use the health record module to gain access to the patient's health record and/or other information related to the patient. The patient's health record may include, among other things, prior medical history, medications, familial history (including hereditary/genetic information), lifestyle information, and test results. The patient may cause utilize the health record module to perform actions related to the health record. For example, the patient may view a list of medications that have been taken and/or are currently being taken by the patient. When a refill is needed, the patient may submit a refill request to the doctor electronically. The health record module may therefore be used by the patient in order to immerse the patient in the healthcare experience, which may enhance the patient's interaction with the doctor.

To help maintain appointments, the patient may use the appointment module to create, view, and/or otherwise facilitate management of appointments. The patient may use the appointment module to schedule a new appointment, view a schedule of appointments, cancel or modify an appointment, view past appointments, and/or perform other actions related to appointments. By providing an online interface for scheduling appointments, patient accessibility to the doctor may be enhanced.

The appointment module may use the social networking module to enable a user to track appointments and rate a doctor. According to an aspect of the invention, the appointments module may display an appointment with related comments and/or messages between the doctor and the patient. For example, upon completing an appointment, the doctor may send a message to the patient asking for updates. The patient may respond to the message with an update. When displaying the appointment, the appointment module may display messages associated with the appointment. By providing the patient with the capability to view historical patient appointment information, the appointment module may enable the patient to, among other things, rate their experiences with the doctor and refresh their memory regarding a particular appointment. For example, upon recently completing an appointment with a doctor, the appointment module may use the social networking module to conduct a survey requesting patient feedback for the doctor, leveraging social network tools in order to rate doctors in the system.

According to an aspect of the invention, the patient may use the billing module to interact with account and billing information for the patient. The billing module may be used to update personal information of the patient such as, among other things, contact information, payment methods, and insurance information. Alternatively or additionally, the billing module may be used to, among other things, view billing information (such as itemized listing of services—such as per message, per web-chat, per office visit, etc., and their fees), pay doctor fees, and pay system usage fees. In this manner, the patient may manage aspects of the patient's account and billing system using an integrated, real-time, display. According to an aspect of the invention, the billing module may facilitate a payment plan between a patient and the patient's doctor (and/or team of doctors). For example, a patient may pay the doctor on a per-visit basis, which may be facilitated by the billing module (i.e., the billing module may accept payments by a patient on behalf of the doctor). Payments may be processed electronically via credit card transactions, online payment services such as PAYPAL, and/or other electronic transactions. Alternatively or additionally, the billing module may be configured such that certain payments via the billing module are not expected by the patient but instead paid by the patient directly to the doctor. In this manner, the system provides patients with a flexible payment capability.

According to an aspect of the invention, a patient may use the notifications module to interact with and view notifications for the patient. Notifications may include, among other things, reminders of upcoming appointments, reminders of upcoming medication refill dates, important notifications from the doctor (such as the aforementioned patient group notices), various communications (e-mail, chat, SMS, etc.), referrals, and aforementioned lab report availability notifications. For example, the doctor may refer the patient to a specialist in order to get a second opinion. The referral may include information related to the specialist. Upon receiving a selection of a specialist, the notification module may cause various operations to be performed such as, for example, schedule an appointment with the specialist, display profile information for the specialist, and display user ratings for the specialist.

According to an aspect of the invention, a patient may use the experts module to view and manage a team of experts for the patient. The team of experts may include, among other things, doctors, specialists, and consultants for which the patient has authorized personal information (pertaining to the patient) to be shared and/or discussed amongst each member of the team of experts. One or more members of the team of experts may also be part of the system such that the patient may communicate and make appointments with the team of experts.

According to an aspect of the invention, the patient may use the experts module to search for experts to add to the team of experts. A search results display may list each expert alongside (or otherwise adjacent to) an avatar representing the expert. The experts module may include expert profile information for review by the patient, thereby providing the patient with information by which to determine whether to add the expert to the team of experts. By adding the expert to the team of experts, the patient may cause the system to grant to the newly added expert permission to, among other things, access the health record of the patient, discuss the patient online with other experts among the team of experts, and contact the patient directly.

According to an aspect of the invention, the system may include an invoice module for managing fees and generating an invoice that may include differential fee calculations based on one or more billing factor(s). For example, a doctor may specify fee information that includes different fees to be charged based on one or more billing factor(s).

Billing factors may include, for example, the medical service performed, a method of interaction between the doctor and the patient when the doctor performs the medical service, a fee rate (such as an hourly fee), a fixed fee (such as predefined fees regardless of time), and/or other billing factors. Medical services may include, for example, a routine checkup, a consultation for diagnosing patient symptoms, a follow-up consultation, a lab test (such as drawing blood, taking x-rays, etc.) and/or any other medical service provided by the doctor. As previously noted, methods of interaction may include virtual methods, in-person methods, or any other methods by which a doctor may interact with a patient. A doctor may charge a different fee for different medical services, different methods of interaction, different fee rates, and/or different fixed fees, which may be managed by invoice module.

According to an aspect of the invention, a billing factor may be used alone or in combination with other billing factors. In this manner, a doctor may specify various fees to be charged based on one or more billing factors. The invoice module may use the one or more billing factors to automatically generate a bill for the doctor based on the medical service that was performed, the method of interaction by which the medical service was performed, whether a fee rate should be applied, and/or whether a fixed fee should be applied.

When a billing factor is used alone, invoice module may generate an invoice based on a single billing factor. For example, a billing factor may specify a particular fee for a particular medical service provided by the doctor. In other words, each medical service may be associated with a particular fee for that service. Alternatively or additionally, a billing factor may specify a particular fee based on a method of interaction with the doctor. Thus, a particular fee may be charged based on the method of interaction in which the doctor performs a medical service. As such, the doctor may specify a particular fee for an email and a different fee for an in-person consultation. Alternatively or additionally, a billing factor may specify a particular fee based on a fee rate that is charged according to a time increment. Time increments may be, for example, by hour, by minute, and/or any other time increment. By using a fee rate billing factor, a fee may be calculated according to a billing factor based on the amount of time the doctor spends interacting with or otherwise performing a medical service on the patient. Alternatively or additionally, a billing factor may specify a fixed fee for services provided by the doctor.

By using a combination of these features, various parties benefit. For example, a website operator providing a website implementing the system may generate various fees from doctors and patients using the website. A doctor may subscribe to the website in order to manage existing patients, find new patients, and join the website's network of doctors who have already subscribed, thereby expanding the doctor's referral network. A patient may subscribe to the website in order to find doctors subscribed to the website and become more actively involved in the overall healthcare experience. Once found, the patient may pay the doctor for the doctor's services as well as subscription fees to the website operator, which may be facilitated by the website. As discussed above, the patient may pay the doctor for services using a pay-as-you-go payment method, thereby providing the patient with flexible payment terms on a per-visit basis. By using the website, the patient may gain enhanced interaction with the doctor, the patient's health records and other patient information, thereby immersing the patient in the overall healthcare experience.

Other objects and advantages of the invention will be apparent to those skilled in the art based on the following drawings and detailed description.

DETAILED DESCRIPTION

Figure 1:
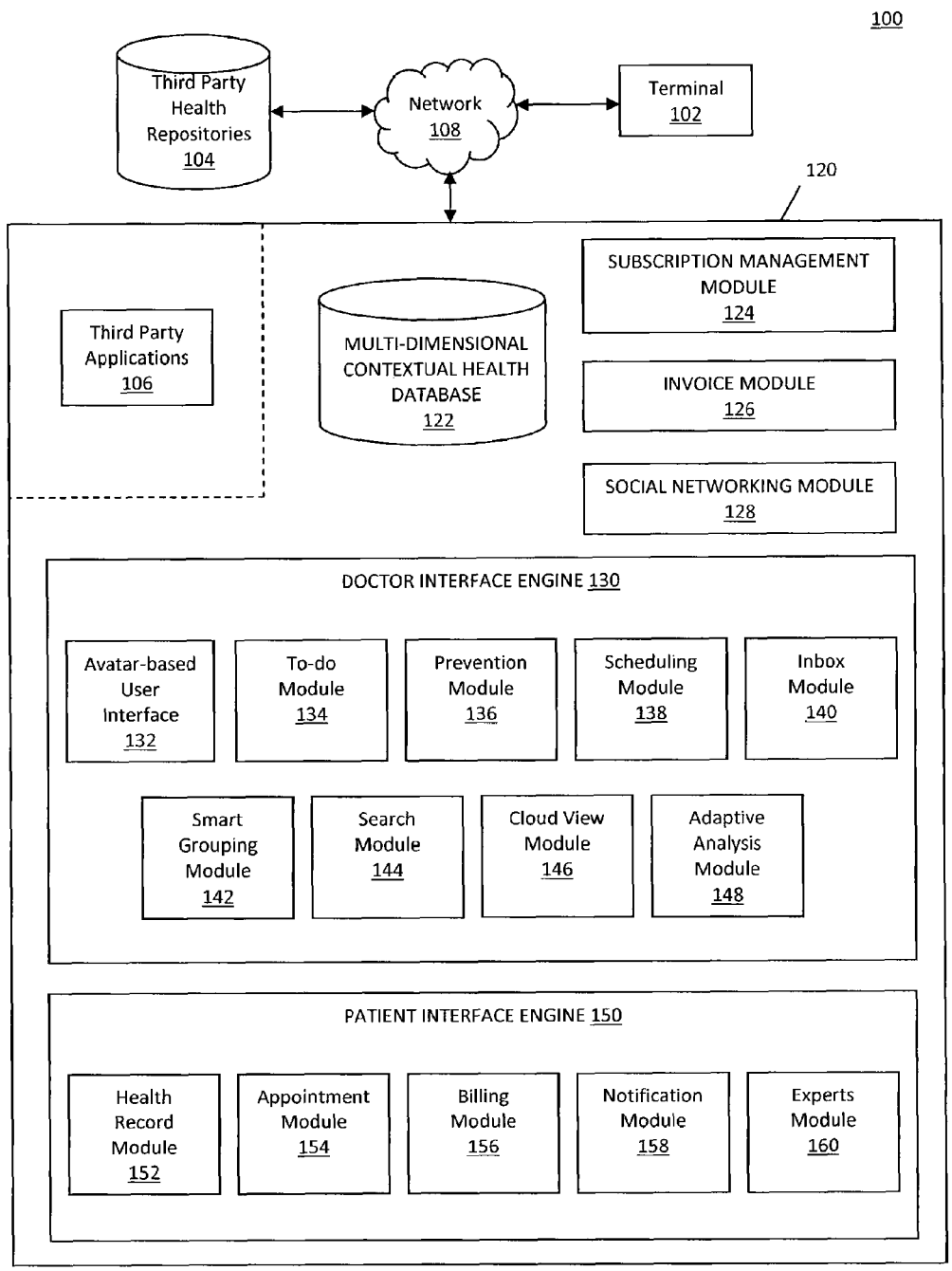
FIG. 1 illustrates a block diagram of an exemplary system for providing a multi-dimensional contextual platform for managing a medical practice, according to an aspect of the invention.

According to an aspect of the invention, FIG. 1 illustrates a block diagram of an exemplary system 100 for providing a multi-dimensional contextual platform 120 for managing a medical practice. The multi-dimensional contextual platform 120 may be used to, among other things, manage, diagnose, and communicate with patients in a medical practice. The multi-dimensional contextual platform 120 may comprise an Internet web site, an intranet site, or other application hosted, for example, on one or more servers. According to an aspect of the invention, the multi-dimensional contextual platform 120 may be accessible over a network 108, via any wired or wireless communications link, using one or more user terminals (120). Network 108 may include any one or more of, for instance, the Internet, an intranet, a PAN (Personal Area Network), a LAN (Local Area Network), a WAN (Wide Area Network), a SAN (Storage Area Network), a MAN (Metropolitan Area Network), or other network. Examples of terminal 120 may include any one or more of, for instance, a personal computer, portable computer, personal digital assistant (PDA), workstation, web-enabled mobile phone, WAP device, web-to-voice device, or other device. Those having skill in the art will appreciate that the invention described herein may work with various system configurations.

The multi-dimensional contextual platform 120 may include dynamic, avatar-based interfaces, generated by a doctor interface module 130 and a patient interface module 150. The multi-dimensional contextual platform 120 may also include a social networking module 180 to, among other things, facilitate doctor and patient online communication, which may be in real-time, thereby enhancing the overall healthcare experience. Online communication may include, for example, email, instant message, online comments, voice conference, and video conference.

According to an aspect of the invention, the system 100 may include a multi-dimensional contextual database 122 for storing a patient's medical records and other patient information. The website may incorporate or otherwise use information from the multi-dimensional contextual database 122, third party health repositories 104, and/or other sources of information. A dimension represents an aspect of the patient's medical record and may include, among other things, Medical Conditions, Office Visits, Medications, Test Results, and Imaging Results. Each dimension may include information elements, which represent information from the patient's medical record. For example, information elements that contextually form part of the Medical Conditions dimension may include particular medical conditions (e.g., asthma, eczema, headaches, etc.) suffered by the patient. Information elements that contextually form part of the Medications dimension may include particular medications being taken by the patient, medications that the patient has taken, and/or any other medication associated with the patient.

According to an aspect of the invention, an information element may be viewed in multi-dimensional contexts. For example, when viewed in the context of the Medical Conditions dimension, asthma may be displayed among other medical conditions suffered by the patient. When asthma is viewed in the context of the Medications dimension, which may otherwise display all medications for the patient, medications being taken for asthma may be displayed. As a further example, when asthma is viewed in the context of the "Office Visits" dimension, office visits during which asthma symptoms were presented may be displayed. Thus, by providing a multi-dimensional view of information from the health record of a patient, information from a medical record may be viewed according to the context in which the information is presented.

According to an aspect of the invention, an information element may be linked to another information element. For example, an information element "diabetes" may be linked to another information element "diagnosis" such that the medical condition diabetes is linked to the diagnosis in which diabetes was made. In turn, "diagnosis" may be linked to an information element "test results," for example, such that the test results forming the basis of the diagnosis may be linked to the diagnosis. In this manner, a multi-dimensional, contextual database 122 may provide comprehensive information on which displays and analyses may be generated and performed.

According to an aspect of the invention, an information element may be categorized into an information element category. For example, lab results relating to blood workups may be categorized as a "hematology" category. In this manner, information elements may be viewed in the context of similar information elements and grouped accordingly, thereby helping the doctor to organize information from a patient's health record.

According to an aspect of the invention, the system 100 may include a doctor interface module 130 for assisting the doctor in managing a medical practice. The doctor interface module 130 may include an avatar-based user interface 132, a to-do module 134, a prevention module 136, a scheduling module 138, an inbox module 140, a smart grouping module 142, a search module 144, a cloud view module 146, an adaptive advisor 148, and/or other modules.

According to an aspect of the invention, the multi-dimensional contextual platform 120 may depict patients and doctors as avatars, personalizing doctor-patient online interactions. An avatar may include a real (e.g., photo) or virtual representation of a user (e.g., doctor, patient, and/or other individual or entity interacting with the system). Representations may include, among other things, an image (e.g., photograph, graphic, etc.), text, color, audio file, and/or any combination of representations.

According to an aspect of the invention, the avatar-based user interface 132 may display a number of avatars representing patients, prospective patients, colleagues, and/or other individuals or entities relevant to the doctor's practice. For example, the number of displayed avatars may represent a portion of patients or all patients in the doctor's practice, thereby providing a snapshot view of patients under the doctor's care. The doctor may use the avatar-based user interface to 132 view and interact with, among other things, communications from patients, test results for patients, appointment schedules, smart grouping of patients, and comprehensive analyses of medical records based on multiple dimensions of the patient in view of contextual information. The comprehensive analyses may assist the doctor to more effectively diagnose, treat, and manage care for each patient.

According to an aspect of the invention, the avatar-based user interface 132 may display patient events associated with patients in real-time. Patient events may include recent or otherwise noteworthy information related to the patient in which the doctor may be interested. A patient event may be displayed adjacent to (or otherwise associated with) an avatar representing the patient. Patient events may include, among other things, recent communications from patients, test results, and upcoming appointments. According to an aspect of the invention, a patient event may be indicated using a patient event indicator associated with a patient's avatar. The patient event indicator may be depicted using thought bubbles, graphic, text, and/or other display techniques, or a combination thereof. Alternatively or additionally, a patient event indicator may include a blinking avatar. A patient event indicator may include a description of a patient event, a preview of a patient event, and/or link to a patient event. For example, when a patient event includes a message from a patient, the entire message, a portion of the message, or a link to the message may be indicated by the patient event indicator. As such, clicking (or otherwise selecting) a patient event indicator may cause the avatar-based user interface 132 to retrieve more detailed information for the patient event (such as retrieving an entire message from a patient). In this manner, the doctor may be notified of patient events as they occur, thereby enabling the doctor to respond to patient events in real-time and facilitating management of the doctor's practice.

As discussed above, patient events may be displayed (or posted) in real-time. For example, when an instant message (or other communication) from a patient is communicated to the doctor while the doctor is interacting with avatar-based user interface 132, the instant message may appear in a thought bubble adjacent to the sending patient's avatar in real-time. Similarly, recently received lab results for a patient, for example, may appear in a thought bubble adjacent to that patient's avatar. In this manner, the avatar-based user interface 132 may be used by the doctor to, among other things, manage his practice using an integrated display of his patients that highlights patient events in real-time using a familiar and personalized interface.

According to an aspect of the invention, the doctor interface module 130 may include a to-do module 134 for maintaining and displaying various tasks (or to-do) items for the doctor. To-do items may include items to be scheduled or performed by the doctor such as, among other things, schedule a lab test for a patient, send the patient a message asking how the patient is feeling, schedule a consultation with another doctor, and/or other tasks. The to-do module 134 may display a to-do item adjacent to an avatar representing the user associated with the to-do item. The to-do item may be selectable such that a selection of a to-do item may cause the inbox module to schedule and/or perform the to-do item. For example, if a to-do item includes a reminder to send a message to a patient, selection of the to-do item may cause the inbox module 140 to generate or otherwise display an email interface (or other communication interface such as chat, SMS, etc.). A doctor or other user may enter a to-do item for a patient, which is displayed by the to-do module 134, and/or otherwise view and manage to-do items.

According to an aspect of the invention, the doctor interface module 130 may include a prevention module 136 for helping the doctor manage preventative care for patients. The prevention module 136 may display preventative maintenance information related to preventative care for a patient. For example, the prevention module 136 may display preventative maintenance information that includes items that should be performed such as, for example, vaccinations, annual tests, regular checkups, and other preventative healthcare items. As each preventative healthcare item is performed, a checkmark (or other indicator) may convey that the item has been fulfilled, thereby helping the doctor manage preventative healthcare for patients. As another example, the prevention module 136 may display one or more standard growth curves and one or more actual growth curves for a child patient, including the growth progression of the child patient in relation to a standard growth curve. In this manner, the doctor may use the prevention module 136 in order to maintain preventative healthcare for the patient.

According to an aspect of the invention, the doctor interface module 130 may include a scheduling module 138 for helping to create, maintain, and display the doctor's schedule. A doctor's schedule may include tasks that have already been scheduled to be performed on particular dates such as, among other things, a house call, instant message visit, video visit, and/or office visit. According to an aspect of the invention, scheduled tasks may be visually depicted based on the type of task to be performed to help the doctor identify the scheduled task. Visual depictions may include, among other things, icons, shapes, colors, images, text, and/or other visual depictions. For example, a scheduled phone call with a patient may be represented by a telephone icon while a house call visit with a patient may be represented by a house icon.

According to an aspect of the invention, the scheduling module 138 may display scheduled tasks using various interfaces such as, for example, an avatar-based list, a calendar, and a geographic map. The avatar-based list may display a listing of scheduled tasks, and an avatar corresponding to each task listing may be displayed alongside the corresponding listing. The calendar view may present scheduled tasks in a calendar format, where a date and/or task may be selectable to view more detailed information regarding the selected date and/or task.

According to an aspect of the invention, the scheduling module 138 may interface and/or integrate with one or more third party applications 106 in order to display scheduled tasks using a geographic map. For example, scheduled tasks may be overlaid onto a geographic map using online mapping applications (e.g., GOOGLE MAPS, MICROSOFT LIVE, etc.) in order to display a location where each scheduled task is to be performed. The doctor may use the mapped tasks, for example, to view a route of house visits, and/or to get directions. In particular, when overlaying scheduled tasks onto a geographic map, scheduled tasks may be displayed according to their type. In this manner, the scheduling module 138 may be used by a doctor to efficiently time-manage patient visits (or other interactions) by using various visual interfaces.

According to an aspect of the invention, the doctor interface module 130 may include an inbox module 140 for displaying patient communications in real-time. Patient communications may include, among other things, general emails from patients, updates from patients, consultations from other doctors, and notifications regarding the availability of information.

General emails from patients may include any email from a patient.

Updates may include messages from patients regarding progress related to the patient (e.g., efficacy of medications, whether the patient is feeling better, etc.).

Consultations may include messages from a specialist who may have been consulted to give their opinion of the patient. For example, a specialist may have reviewed the medical record of the patient and/or examined the patient in order to provide an opinion for the doctor to consider.

Notifications may include communications informing the doctor of the availability of information such as, among other things, lab results from a laboratory and medical records from another doctor. For example, a doctor may receive a notification that lab results for a patient are available. According to an aspect of the invention, upon reviewing the lab results, the doctor may approve the release of the lab results for review by the patient, which may cause the system to notify the patient that the lab results are available for review. By providing an integrated interface to various patient communications related to the patient's medical treatment, the inbox module 140 may enable the doctor to make informed decisions based on information as it becomes available in real-time.

According to an aspect of the invention, the doctor interface module 130 may include a smart grouping module 142 that generates and maintains patient groups. A new patient group definition, which describes a patient group, may be generated manually by the doctor, automatically by the smart grouping module according to a dimension, and/or automatically by the smart grouping module 142 according to a common characteristic shared among patients in the patient group (e.g., patients taking the same medication or having the same medical condition). In this manner, the doctor may identify and manage patients according to one or more shared characteristic(s) that are common among a group of patients.

According to an aspect of the invention, the smart grouping module 142 may add patients to a smart group based on the method in which the smart group was created. For example, the doctor may identify a patient as being at-risk of, or suffering from, diabetes and add the patient to the diabetes group by dragging an avatar representing the patient to a folder representing the diabetes group, or by otherwise indicating that the patient belongs to the diabetes patient group. Alternatively or additionally, the smart grouping module 142 may automatically place the patient in the diabetes patient group based on an indication in the patient's medical record that the patient suffers from diabetes. Thus, the smart grouping module 142 may be used to easily add patients to various patient groups, which enables the doctor to interact with patients on a group level.

According to an aspect of the invention, a doctor may identify or otherwise select a patient group to be managed. Once a patient group has been identified or otherwise selected, the doctor may perform subsequent actions for the selected group. Subsequent actions may include sending a group message, sending the members of the group literature on a health topic, and/or perform other action suitable for a group. For example, the doctor may select a "LIPITOR"

patient group, and send a group message that a cheaper generic version of the drug is currently available. In another example, the doctor may select the "diabetes" group and send the group medical literature that includes relevant information for diabetes sufferers. In this manner, the smart grouping module 142 may be used to perform actions on a group of patients that would otherwise be redundantly performed for each patient in the group on an individual basis.

According to an aspect of the invention, the multi-dimensional contextual platform 120 may include a search module 144 for enabling searching for patients by patient group, by dimension, or individually. The search module 144 may auto-complete search terms (such as letters, words, numbers, etc.) as the search terms are being received. According to an aspect of the invention, the avatar-based user interface 132 may integrate search results into the display, where patients identified by search results may be dynamically highlighted. Highlighting may include, for example, focusing avatars of patients in the search results to the foreground while fading other avatars to the background. Alternatively or additionally, highlighting may include enlarging, coloring differently, or otherwise altering the appearance of avatars of patients in the search results but not other avatars.

For example, a doctor may search a Medical Conditions dimension by entering search terms. As the doctor enters search terms that are recognized (such as "diabet"), the search module 144 may auto-complete the entered search terms to the recognized term (such as "diabetes"). Once recognized, the avatar-based user interface 132 may focus the avatars representing patients in the diabetes patient group to the foreground while fading avatars not in the diabetes patient group to the background. In another example, a doctor may search names of patients by entering at least a portion of a name of the patient of interest. Patients whose names matches the search terms may be focused to the foreground while patients with non-matching names are faded to the background. The process may be dynamic such that as search terms are added (e.g., the doctor inputting letters), search results may be filtered such that highlighted patients who are no longer in the search result are faded to the background. For example, by entering "John" all patients named "John" may be highlighted, while adding "John A" moves patients whose last name does not begin with "A" to the background. In this manner, the search module 144 may enable a doctor to dynamically find and highlight particular patients using a familiar avatar format. A doctor may search for and dynamically view results of search terms to find a patient, group of patients, and/or other information in the system.

According to an aspect of the invention, a highlighted avatar or group of avatars in the search result may be selected for further processing. In other words, further processing may be performed on an individual avatar or group of avatars after the individual avatar or group of avatars have been identified by the search module. For example, clicking (or otherwise selecting) an avatar may result in the generation of a patient preview display. The patient preview display may show a preview of the patient's medical record. The doctor may configure the information that is displayed in the patient preview. Clicking on (or otherwise selecting) a patient group may result in a group action to be performed as discussed above.

According to an aspect of the invention, clicking (or otherwise selecting) an avatar may cause the doctor interface module 130 to generate a patient view for displaying the medical record of the patient. The patient view may be accessed by clicking (or otherwise selecting) an avatar representing the patient, by executing a search using terms that identify the patient (e.g., the patient's name, unique system identifier for the patient, or other identifying criteria), by selecting a link from the patient preview, and/or by otherwise identifying a patient of interest. The patient view may be used to interact with various dimensions of the health records of a patient, view analyses of the medical record, and communicate with the patient.

According to an aspect of the invention, the doctor interface module 130 may include a cloud view module 146 for displaying one or more focal points of interest of a patient, around which information related to the focal point may be arranged. The cloud view module 146 may display a focal point at any position in the display (such as, for example, at the center of the display). A focal point may include a dimension of a patient's medical record around which information elements are arranged. For example, when viewing the "medications" dimension of a patient, "medications" may be a focal point around which the drug LIPITOR and/or other medications associated with the patient are arranged. Alternatively or additionally, a focal point may be an information element around which dimensions and/or other information elements are arranged. For example, when displaying the information element LIPITOR, the cloud view module 146 may display LIPITOR as a focal point, around which dimensions related to LIPITOR are arranged. Dimensions may include Office Visits during which LIPITOR was prescribed (or discussed), Medical Conditions that LIPITOR addresses and/or any other dimensions associated with LIPITOR. In another example, LIPITOR may be a focal point around which other information elements are arranged, such as a particular Lab Result information element that is associated with the actual diagnosis of the medical condition that led to prescribing LIPITOR. Thus, the cloud view module 146 may be used to focus on particular aspects of the patient's health record in multi-dimensional contexts while highlighting important aspects of the patient's health record.

According to an aspect of the invention, the cloud view module 146 may display dimensions and information elements using graphical elements including, for example, geometric shapes, text, colors, images, other graphical visualizations, and/or other graphical elements. For example, an information element may be depicted as a circle with text that describes the information element displayed adjacent to, within, or on the circle.

According to an aspect of the invention, the cloud view module 146 may vary the size, color, shape, and/or spatial arrangement of a dimension and/or information element using display rules. The display rules may be based on information element properties, which may include information from the medical record of the patient related to an information element such as, for example, severity of a medical condition, frequency that a medication is administered, and number of office visits within a given time period. For example, a rule may be created that may cause the cloud view module to color an information element "eczema" red (or alter appearance in another manner) when a patient suffers from a severe form of eczema. Alternatively or additionally, a rule may be created that causes the cloud view module to vary the spatial arrangement of the information element along first and second axes of the cloud view depending on the properties of the information element. For example, the cloud view module 146 may vary a distance from a focal point to an information element based on a display rule. In this manner, the cloud view may be used to graphically emphasize various properties of information elements for each dimension of a patient's medical record, which may be used to treat and manage the patient accordingly.

According to an aspect of the invention, the doctor interface module 130 may include an adaptive advising module 148 for adaptively analyzing the medical record of a patient in order to advise the doctor of potential diagnoses, prognoses, and/or suggested courses of action for a patient. The adaptive advising module 148 may continuously integrate diagnostic information in order to generate diagnoses and/or suggested courses of action. The diagnostic information may include, among other things, clinical history, prior doctor examinations of the patient, medications, test results, and prior patient outcomes. The diagnostic information may originate from the patient's health record and/or third party health repositories 104 that include information from various patients. The adaptive advising module 148 may adapt suggestions based on input from the doctor refining the suggestions and/or based on information that has been added since a suggestion was made (such as a new test result or efficacy of a suggested drug). In other words, as the treatment of the patient progresses, the adaptive advising module 148 may also adaptively make suggestions based on new information. In this manner, the adaptive advising module 148 may be used to help the doctor diagnose, generate prognoses, and/or treat the patient.

According to an aspect of the invention, the multi-dimensional contextual platform 120 may include a patient interface module 150 for enhancing patient interaction with the doctor, with the patient's health records, and with other information. The patient interface module 150 may provide the patient with enhanced accessibility to the doctor via instant-messaging (chat), SMS, e-mail, voice conferencing, video conferencing, web forms, and/or other communications techniques. The patient may use the patient interface module 150 in order to, among other things, receive reminders regarding treatment (e.g., prescription refills, upcoming doctor appointments, etc.), view billing information, view test results, and locate specialists. The patient interface module 150 may include a health record module 152, an appointment module 154, a billing module 156, a notifications module 158, an experts module 160, and/or other modules.

According to an aspect of the invention, the health record module 152 may provide the patient with access to the patient's health record and/or other information related to the patient. The patient's health record may include, but is not limited to, prior medical history, medications, familial history (including hereditary/genetic information), lifestyle information, and test results. A patient may use the health record module 152 to perform actions related to the health record. For example, a patient may view a list of medications that have been taken previously, and/or are currently being taken by the patient. When a refill is needed, the patient may submit a refill request to the doctor electronically. Upon receiving notification that the request has been fulfilled, the notification module 158 (discussed further below) may transmit a message to the patient that the medication has been filled and is awaiting patient pickup at a pharmacy that is associated with the patient. Alternatively or additionally, the doctor may fill the prescription using an online pharmacy, for example, in response to the refill request.

According to an aspect of the invention, when a test result is available, the patient may view the test result, which may include explanatory notes, for example, made by the doctor. As previously noted, the doctor may approve release of the test result to the patient before the health record module 152 displays the test result to the patient. In other words, the health record module 152 may be configured to display a health record to the patient when the patient is authorized (by the doctor, for example) to view the health record. The health record module may therefore be used by the patient in order to immerse the patient in the healthcare experience, which may enhance the patient's interaction with the doctor.

To help a patient maintain appointments, the patient may use the appointment module 154 to create, display, and/or otherwise facilitate management of appointments. The patient may use the appointment module 154 to schedule a new appointment, view a schedule of appointments, cancel or modify an appointment, view past appointments, and/or perform other actions related to appointments. When creating or otherwise scheduling a new appointment, a patient may view available appointment times and/or enter various information related to the new appointment. For example, appointment module 154 may provide an input for specifying one or more reason(s) for the appointment, which may be noted on the new appointment, thereby apprising the doctor of the reason(s) for scheduling the appointment. Alternatively or additionally, appointment module 154 may provide a selectable list of methods by which the new appointment is to be conducted. System 100 provides various methods by which the patient may interact with the doctor. As such, a patient may schedule an appointment by specifying one or more method(s) of interaction. Methods of interaction may include virtual methods, in-person methods, or any other method by which a doctor may interact with the patient. For example, a patient may wish to schedule an appointment to interact with the doctor by a virtual method such as via online communication (e.g., email, instant message, comments, voice conference, video conference, etc.) and/or via in-person method (e.g., telephone, house call, in-office, etc.). As such, appointment module 154 may display a list of methods by which the new appointment is to be scheduled, thereby providing the patient with a flexible method to schedule an appointment to interact with the doctor. By providing an online interface for scheduling appointments, patient accessibility to the doctor may be enhanced.

According to an aspect of the invention, the appointment module 154 may display a listing of appointments for a patient. The patient may view both upcoming and past appointments. Each appointment may include an avatar of the doctor with whom the appointment has been (or was) made. The appointment module 154 may include information for each appointment such as, among other things, the reason for the visit, diagnosis, medications administered, video/audio replays (if available), and other information related to the appointment. In particular, when the appointment is a video conference appointment, the appointment module 154 may display a video file of the video conference appointment.

The appointment module 154 may utilize social networking module 128 by enabling a user to track appointments and rate a doctor. According to an aspect of the invention, the appointments module 154 may display an appointment with related comments and/or messages between the doctor and the patient. For example, upon completing an appointment, the doctor may send a message to the patient asking for follow-up updates. The patient may respond to the message with an update. When displaying the appointment, the appointment module 154 may display messages associated with the appointment. By providing the patient with the ability to view historical patient appointments, the appointment module may enable the patient to, among other things, rate their experiences with the doctor and refresh their memory regarding a particular appointment. For example, upon recently completing an appointment with a doctor, the appointment module 154 may interface with the social networking module 180 to conduct a survey requesting patient feedback for the doctor, thereby leveraging social networking tools in order to rate doctors in the system.

According to an aspect of the invention, the patient interface module 150 may include billing module 156 for displaying billing and account information for the patient. Billing module 156 may be used to update personal information of the patient such as, for example, contact information, payment methods, and insurance information. Alternatively or additionally, billing module 156 may be used to, among other things, view billing information that may include an itemized listing of charges from services, pay doctor fees, and pay system usage fees. The itemized charges may provide information related to the method by which each service was performed such as per email message, per instant message, per office visit, etc., and their associated fees. In other words, each fee for each service may vary based on the method in which the patient interacted with the doctor. As previously noted, charges may vary based on the method of interaction. In this manner, the patient may manage aspects of the patient's account and billing system using an integrated, real-time, display.

According to an aspect of the invention, the billing module 156 may facilitate a pay-as-you-go plan between a patient and the patient's doctor (and/or team of doctors). For example, a patient may pay the doctor on a per-visit basis, which may be facilitated by the billing module. Payments may be processed electronically via credit card transactions, online payment services such as PAYPAL, and/or other electronic transactions. Alternatively or additionally, payments may be processed by the doctor dealing directly with the patient. In this manner, the system provides patients with a flexible payment capability.

According to an aspect of the invention, the patient may use the notifications module 158 to interact with and view notifications for the patient. Notifications may include, for example, reminders of upcoming appointments, reminders of upcoming medication refill dates, important notifications from the doctor (such as the aforementioned patient group notices), various communications, referrals, and aforementioned lab report availability notifications. For example, the doctor may refer the patient to a specialist in order to get a second opinion. The referral may include information related to the specialist. Upon receiving a selection of the specialist, the notification module 158 may cause various operations to be performed such as, for example, scheduling an appointment with the specialist, displaying profile information for the specialist, and displaying user ratings for the specialist.

According to an aspect of the invention, the patient interface module 150 may include an experts module 160 for displaying and managing a team of experts for the patient. The team of experts may include, for example, doctors, specialists, and consultants for which the patient has authorized access to his/her information, which may then be shared and/or discussed amongst each member of the team of experts. One or more members of the team of experts may also be registered with the system 100 such that the patient may communicate and make appointments with each expert. Each expert may be listed alongside (or adjacent to) an avatar that represents the expert. The experts module may include profile information such as, among other things, medical school, specialties, and location, when listing the expert.

According to an aspect of the invention, the experts module 160 may be used to search for additional experts not yet part of the team of experts defined for the patient. Search results may a display of each expert alongside (or otherwise adjacent to) an avatar representing the expert. The experts module 160 may include an expert information profile for review by the patient, thereby providing the patient with information by which to determine whether to add the expert to the team of experts. By adding the expert to the team of experts, the patient may cause the system 100 to grant to the newly added expert permission to, among other things, access the health record of the patient, discuss the patient online with other experts among the team of experts, and contact the patient.

According to an aspect of the invention, system 100 may include a subscription management module 124 that manages subscriptions of doctors and patients. For example, a website operator may implement system 100 as a website to which doctors and patients subscribe in order to facilitate patient care. A doctor may use subscription management module 124 to subscribe to the website in order to manage existing patients, find new patients, and join the website's network of doctors who have already subscribed, thereby expanding the doctor's referral network. A patient may use subscription management module 124 to subscribe to the website in order to find doctors subscribed to the website and become more actively involved in the overall healthcare experience. The website may use or otherwise integrate social networking module 128 in order to provide social network tools. For example, the website may provide the patient with access to ratings of doctors from other patients subscribed to the system, ratings from other doctors subscribed to the system, and/or other individuals or entities that provide ratings for the doctor. In this manner, the patient may make informed decisions when selecting a doctor to receive medical care.

The website operator may also benefit. By using the subscription management module 124, the website operator may manage subscriptions and various fees associated with website usage. For example, the website operator may receive subscription fees from doctors and patients, website usage fees from doctors and patients, licensing fees from doctors (e.g., related to advertising, marketing, technology license fees, etc.), and/or other fees.

Once a patient has been matched to or otherwise has selected a doctor, the patient may use the website in order to schedule an appointment with the selected doctor and receive medical services from the doctor. The patient may pay the doctor for the doctor's services, which may be facilitated by the website (i.e., the website may accept payment from the patient on behalf of the doctor) and/or may be paid by the patient to the doctor directly. As discussed above, the patient may pay the doctor for services using a pay-as-you-go payment method, thereby providing the patient with flexible payment terms on a per-visit basis. According to an aspect of the invention, patient subscription may benefit the patient by, for example, providing reduced fees from subscribed doctors to subscribed patients. For example, the subscription management module 124 may indicate that the patient is a subscribed member, thereby indicating that the patient is to receive a discounted fee relative to another patient who is not subscribed to the website.

According to an aspect of the invention, subscription management module 124 may generate one or more profile(s) for subscribed doctors, subscribed patients, and/or any other user or entity associated with the website. For example, a doctor may provide doctor profile information such as, for example, information related to the doctor's practice, the doctor's background information, fee information, and/or other information. Subscription management module 124 may generate a doctor profile of the doctor that includes the doctor profile information. A patient may also provide patient profile information such as, for example, personal information, reasons for seeking medical care, and/or other information. Accordingly, subscription management module 124 may generate a patient profile of the patient.

According to an aspect of the invention, system 100 may include an invoice module 126 for managing fees and generating an invoice that may include differential fee calculations based on one or more billing factor(s). For example, a doctor may specify fee information that includes different fees to be charged based on one or more billing factor(s).

Billing factors may include, for example, the medical service performed, a method of interaction between the doctor and the patient when the doctor performs the medical service, a fee rate (such as an hourly fee), a fixed fee (such as predefined fees regardless of time), and/or other billing factors. Medical services may include, for example, a routine checkup, a consultation for diagnosing patient symptoms, a follow-up consultation, a lab test (such as drawing blood, taking x-rays, etc.) and/or any other medical service provided by the doctor. As previously noted, methods of interaction may include virtual methods, in-person methods, or any other methods by which a doctor may interact with a patient. A doctor may charge a different fee for different medical services, different methods of interaction, different fee rates, and/or different fixed fees, which may be managed by invoice module 126.

According to an aspect of the invention, a billing factor may be used alone or in combination with other billing factors.

When a billing factor is used alone, invoice module 126 may generate an invoice based on a single billing factor. For example, a billing factor may specify a particular fee for a particular medical service provided by the doctor. In other words, each medical service may be associated with a particular fee for that service. Alternatively or additionally, a billing factor may specify a particular fee based on a method of interaction with the doctor. Thus, a particular fee may be charged based on the method of interaction in which the doctor performs a medical service. For example, the doctor may specify a particular fee for an email and a different fee for an in-person consultation. Alternatively or additionally, a billing factor may specify a particular fee based on a fee rate that is charged according to a time increment. Time increments may be, for example, by hour, by minute, and/or any other time increment. By using a fee rate billing factor, a fee may be calculated according to an amount of time the doctor spends interacting with or otherwise performing a medical service on the patient. Alternatively or additionally, a billing factor may specify a fixed fee for services provided by the doctor.

When a billing factor is combined with one or more other billing factors, invoice module 126 may use two or more billing factors to generate a fee. For example, a billing factor associated with a medical service may be combined with a billing factor associated with a method of interaction with the doctor. In a particular example, a billing factor associated with a follow-up consultation may be combined with a billing factor associated with an email such that a doctor may charge a fee based on both a medical service performed and a method by which the doctor interacts with the patient. In this manner, the doctor may (for example) charge a different fee for a follow-up consultation by email as opposed to a follow-up consultation in-person.

Other combinations of billing factors are contemplated. Furthermore, it should be understood that a billing factor may combine two or more billing factors. In other words, a billing factor may have the effect of two or more billing factors that are combined. For example, a billing factor may be associated with a fee for a follow-up consultation by email and another billing factor may be associated with another fee for a follow-up consultation in-person.

According to an aspect of the invention, a billing factor may provide a weight such that when combining two or more billing factors, one billing factor may be a weight that adjusts a fee associated with another billing factor. The weight may be expressed as a ratio, a fraction, a percentage, and/or any other weight. For example, a billing factor associated with the method of interaction may provide a weight. An email method of interaction may provide a weight (such as 0.2) while an in-person method of interaction may provide another weight (such as 1.0). Each weight may be used to calculate a fee based on a billing factor associated with a medical service (such as a follow-up consultation). In this example, the weights may be applied to the fee by multiplying the weight with the fee to generate a weighted fee. In this manner, invoice module 126 may generate different fees based on different weights.

According to an aspect of the invention, invoice module 126 may receive information related to a doctor's interaction with patients and automatically generate an invoice. For example, a doctor may request to generate an invoice for a patient, in response to which invoice module 126 may query or otherwise receive interactions between the doctor and the patient since the last time an invoice was generated or other appropriate time. For example, invoice module 126 may receive an indication that an in-person diagnostic consultation to address patient symptoms and an email follow-up consultation occurred for the requested invoice. Invoice module 126 may apply the doctor's billing factors in order to generate fees according to the billing factors. As such, by using billing factors, for example, invoice module 126 may automatically generate an invoice for the doctor based on the medical service that was performed, the method of interaction by which the medical service was performed, whether a fee rate should be applied, and/or whether a fixed fee should be applied. It should be understood that an invoice may be generated by invoice module 126 by request, at predefined intervals, and/or any other appropriate time.

According to an aspect of the invention, billing factors may be predefined by a doctor or otherwise suggested by the system using default billing factors. Billing factors may be part of or otherwise be derived from a doctor profile for the doctor (discussed herein elsewhere).

Figure 2:
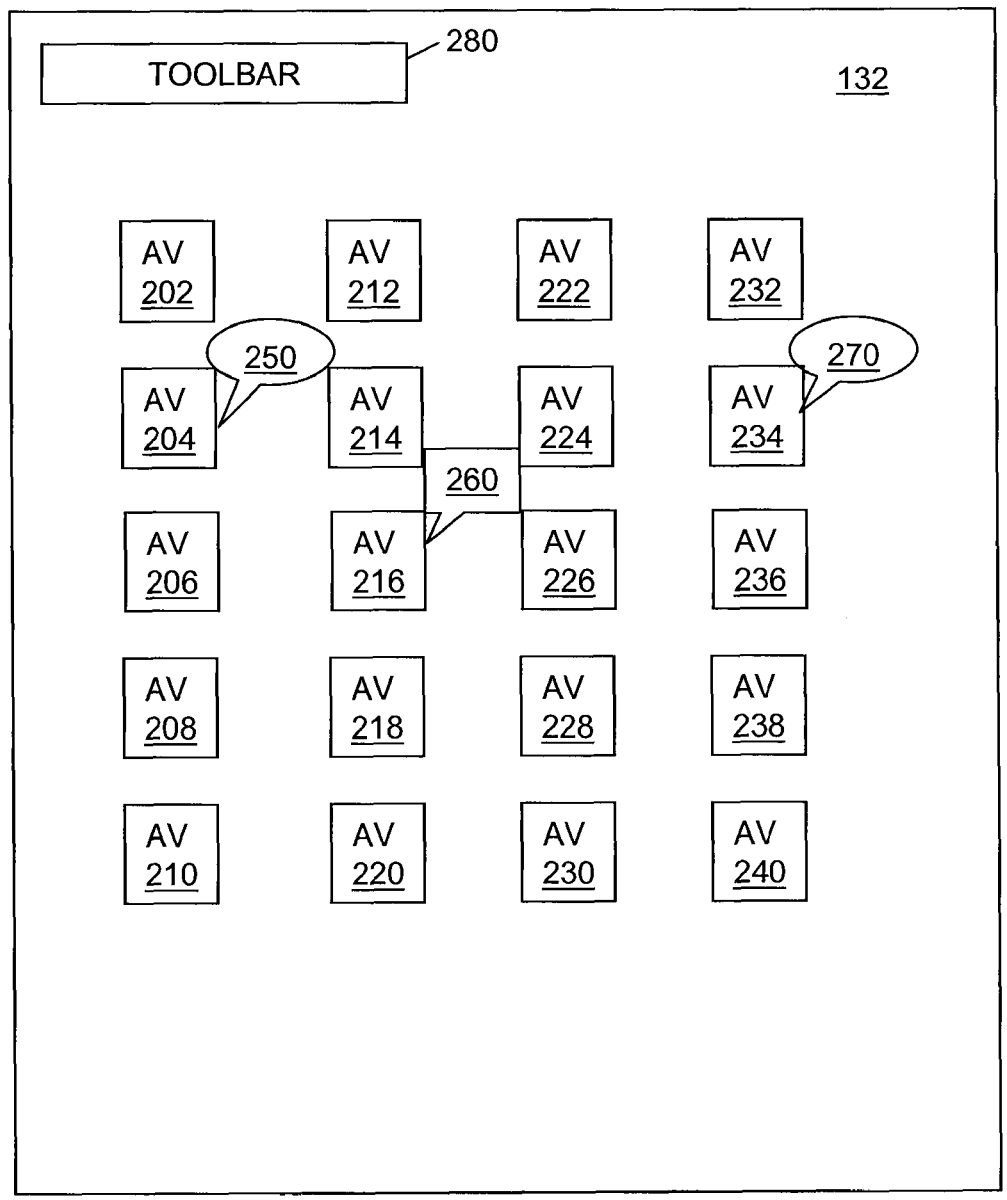
FIG. 2 illustrates a screenshot of an exemplary avatar-based user interface, according to an aspect of the invention.

FIG. 2 illustrates a screenshot of an exemplary avatar-based user interface 132, according to an aspect of the invention. It should be understood that the screenshots described in detail below, and illustrated in the accompanying drawing figures, are exemplary and may differ in appearance, content, and configuration. Further, and as may be described herein, the terms "button," "pull-down menu," "tab," "click-box," "check-box," "hypertext link," and "hot link," are each particular non-limiting examples of a generic "selection portion" which may comprise any known navigational tool that enables users to select, access, display, or navigate through the various views, portions, or modules of the multi-dimensional contextual platform 120. The selection portions may be accessed using any known input device associated with terminal 120 such as, for example, a keyboard, keypad, computer mouse, light stylus instrument, or finger or other body part (in a touch-screen implementation). While a selection portion may be described and illustrated as a button in one implementation, it could comprise a different selection portion (e.g., a check-box) in an alternative implementation. These selection portions may be present in addition to the various navigational tools that may be unique to, or associated with, a web browser that may, in certain implementations for example, be used to access the multi-dimensional contextual platform 120.

Avatar-based user interface 132 may display a toolbar 180, avatars 202-240 representing all or a portion of patients in a doctor's practice, one or more patient event indicators (250, 260, 270), and/or other display items. Toolbar 180 may provide one or more links to various modules associated with doctor interface module 130. In other words, the doctor may use toolbar 180 to access one or more features enabled by one or more of the to-do module 134, prevention module 136, scheduling module 138, inbox module 140, smart group module 142, search module 144, cloud view module 146, adaptive advising module 148, and/or other modules.

The number of avatars displayed may vary as appropriate. Therefore, the number of avatars displayed in FIG. 2 is exemplary only. Avatars 204, 216, and 234 may represent patients that are each associated with a patient event, respectively indicated by patient event indicators 250, 260, and 270. Although illustrated in FIG. 2 as thought bubbles, patient event indicators 250, 260, and 270 may be any shape, graphic, text, etc. As previously noted, patient events may include communications from patients, lab results, or other information related to the patient. For example, a patient represented by avatar 204 may have sent the doctor an instant message, which is indicated by patient event indicator 250. The doctor may click or otherwise select patient event indicator 250 to open an instant message conversation with the patient. The patient represented by avatar 216 may have an appointment with the doctor in 15 minutes (for example), which is indicated by patient event indicator 260. The doctor may click (or otherwise select) patient event indicator 260 to view the appointment with the patient using the scheduling module 138, for example. The patient represented by avatar 234 may have lab results that are recently made available, indicated by the patient event indicator 270. The doctor may click (or otherwise select) patient event indicator 270 to view the lab results. The avatar-based user interface 132 may be used to provide a snapshot display of patients under the doctor's care, incorporating patient events in real-time.

Figure 3:
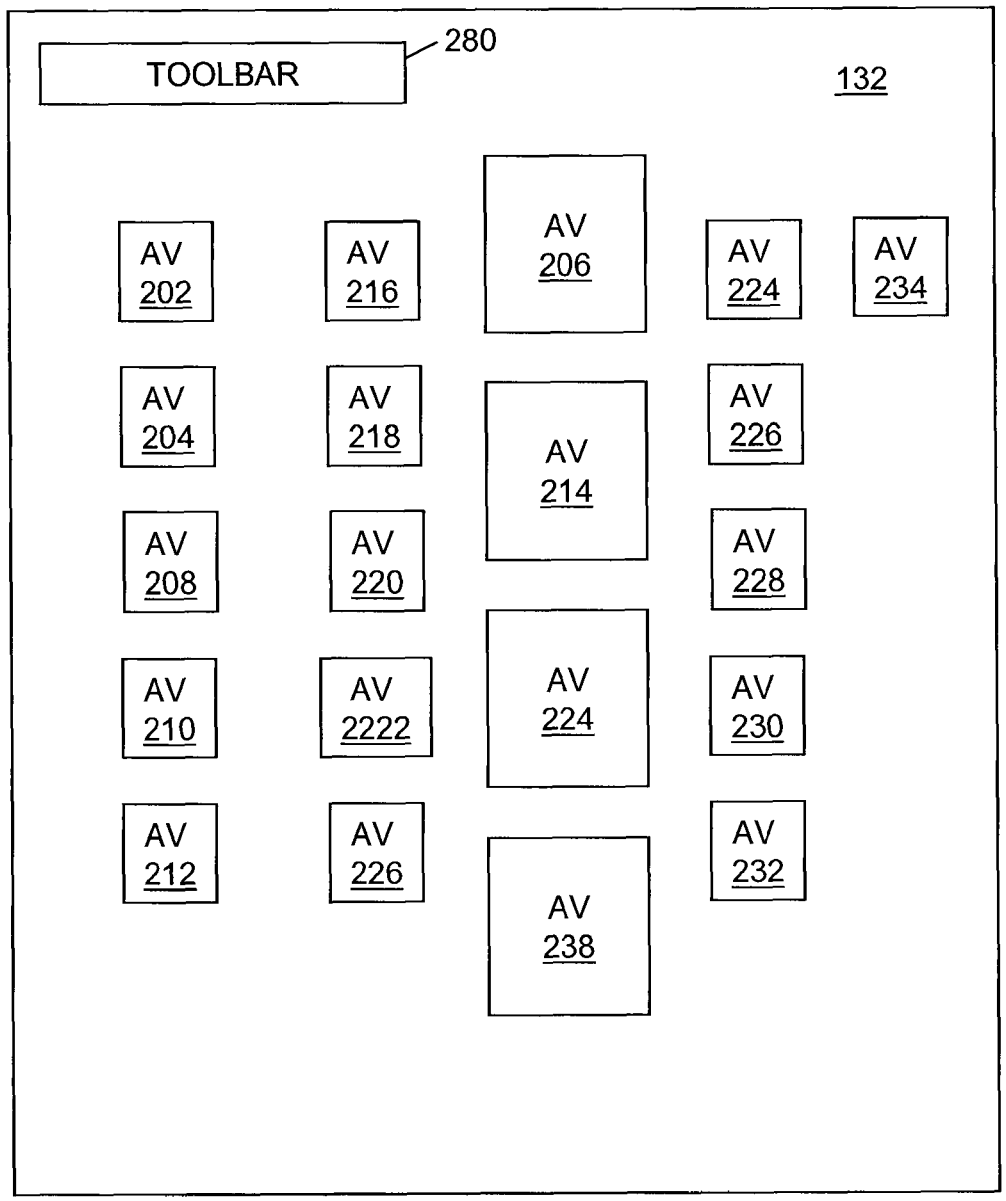
FIG. 3 illustrates a screenshot of an exemplary avatar-based user interface highlighting a group of patients, according to an aspect of the invention.

FIG. 3 illustrates a screenshot of an exemplary avatar-based user interface 132 highlighting a group of patients (e.g., the avatars illustrated in FIG. 2), according to an aspect of the invention. For example, avatars 206, 214, 224, and 238 as illustrated are highlighted by enlarging them and bringing them to the foreground. Avatars 206, 214, 224, and 238 may represent patients belonging to the patient group "diabetes." Upon searching for or otherwise selecting the "diabetes" group, a doctor may cause the avatar-based user interface 132 to highlight avatars 206, 214, 224, and 238. As discussed, highlighting may include other techniques to vary the appearance of the highlighted avatars.

Figure 4:
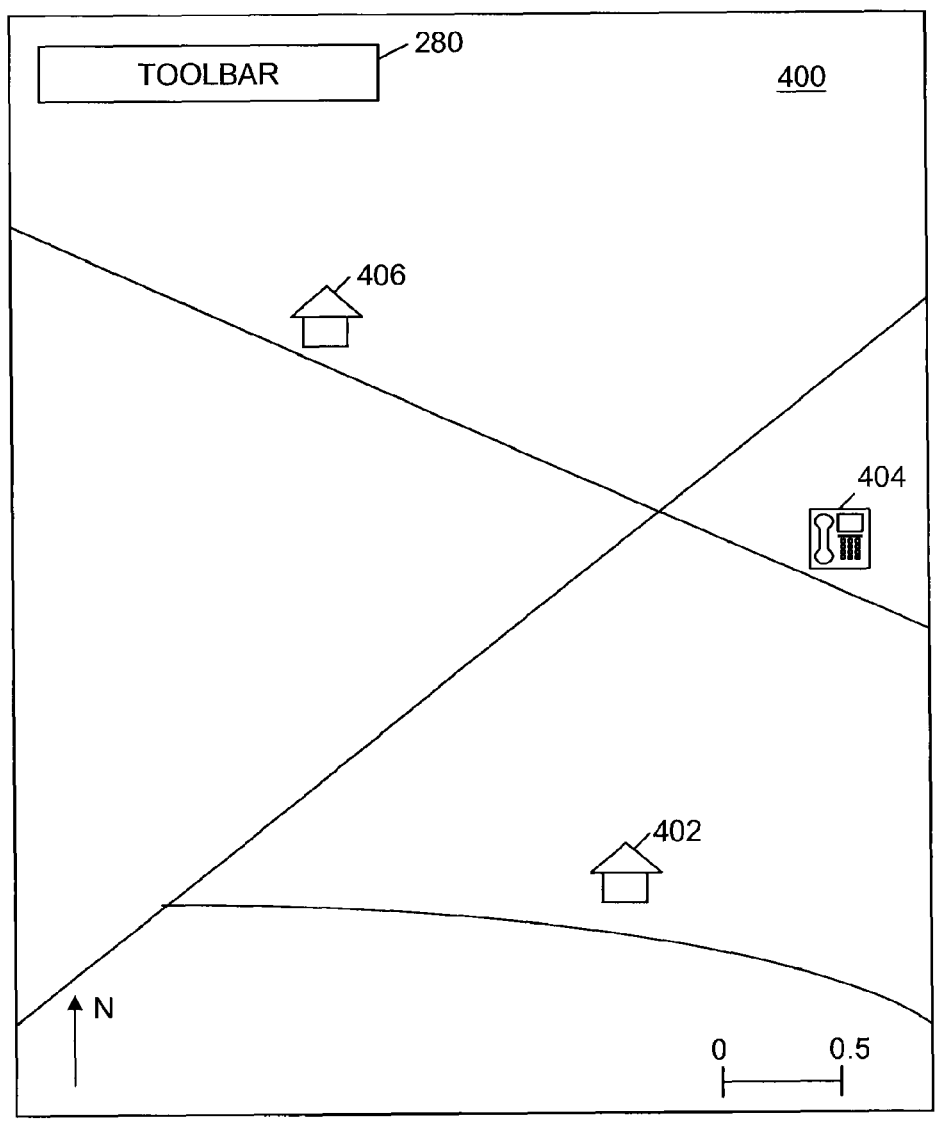
FIG. 4 illustrates a screenshot of an exemplary to-do display for the doctor, according to an aspect of the invention.

FIG. 4 illustrates a screenshot of an exemplary display generated by scheduling module 136 for a doctor, according to an aspect of the invention. In this exemplary illustration, the scheduling module 136 may interface with (or otherwise use) one or more third party applications 106 to generate a map of exemplary appointments 402, 404, and 406. As previously discussed, an appointment may be represented according to a type of appointment. For example, appointments 402 and 406 may represent house calls requiring a doctor to visit the patients at the patients' homes. As such, the scheduling module 136 may represent appointments 402 and 406 as house icons. Appointment 404 may represent a scheduled telephone call with a patient such that the appointment 404 is depicted as a telephone icon. The representations (here, icons) of appointments 402, 404, and 406 may selected by the doctor to get detailed information for the appointment. Details may include the patient name, reasons for the appointment, patient's address, directions, and/or other information related to the patient or appointment. In the illustrated example, a map indicating a route of the house appointments 402 and 406 may be generated. The map may include directions such that the doctor may plan a route of scheduled appointments as necessary.

Figure 5A:
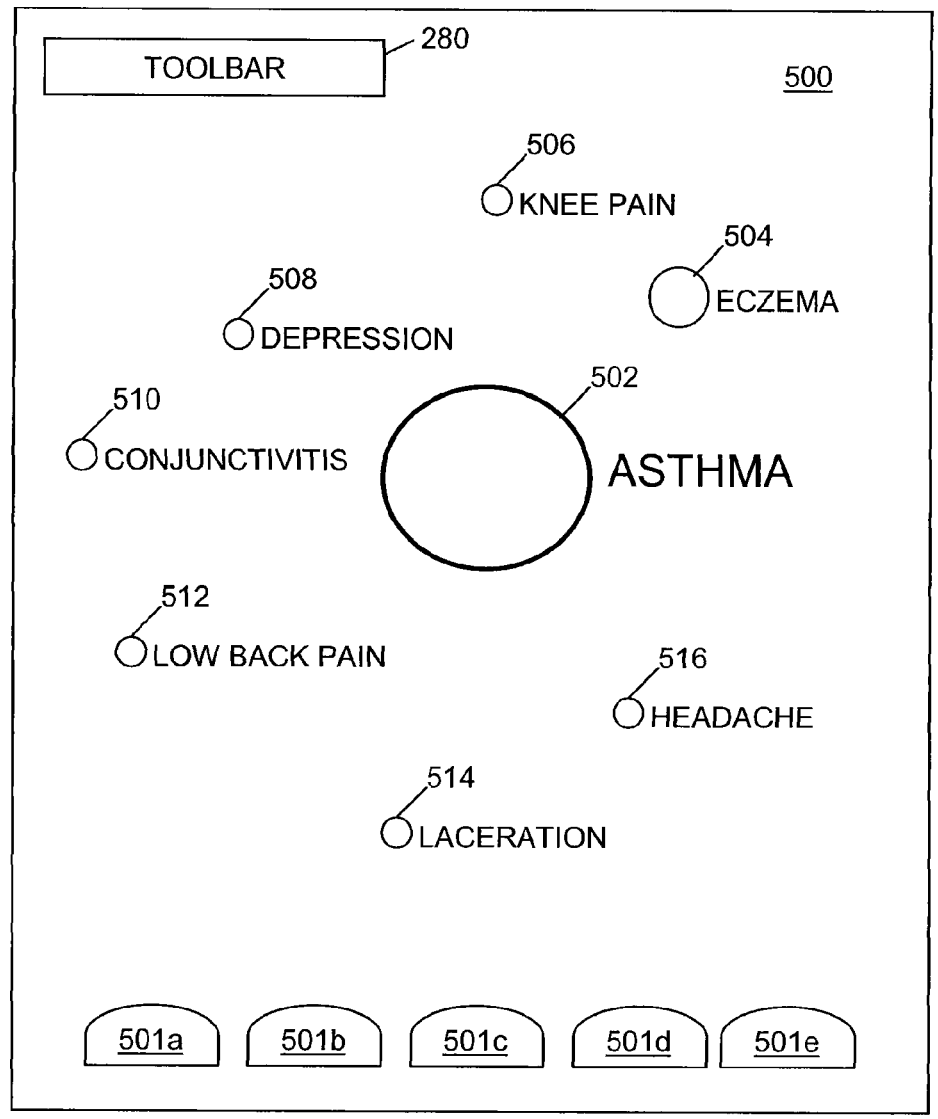
FIG. 5a illustrates a screenshot of an exemplary Medical Conditions cloud view display, according to an aspect of the invention.

FIG. 5a illustrates a screenshot of an exemplary Medical Conditions cloud view 500 displaying the Medical Conditions dimension of the medical record of a patient, according to an aspect of the invention. The Medical Conditions cloud view 500 may display information elements (502, 504, 506, 508, 510, 512, 514, and 516) related to, among other things, health problems, conditions, and diagnoses. For example, information element 502 may represent asthma suffered by the patient and information element 504 may represent eczema suffered by the patient. As discussed above, an information element may have information element properties that result (through the use of display rules) in the display of the information element to be varied. In other words, various information element properties may be used to determine a level of importance (and/or relevance) of one information element relative to another information element. In this example, asthma and eczema information elements 512 and 514 may each have associated information element properties, which may include, for example, a number of interactions (e.g., by virtual or in-person methods described above) with the doctor in which the patient presented symptoms. For example, if the patient presented asthma symptoms ten times as opposed to eczema symptoms four times, the cloud view module may display information element 512 representing asthma as a larger circle, for example, in the Medical Conditions cloud view 500 as compared to information element 514 representing eczema. In other words, asthma may be determined to be more important then eczema for a patient based on a number of interaction with the doctor in which the patient presented symptoms, thereby causing the display of asthma and eczema information elements to differ relative to one another.

Alternatively or additionally, information element properties may relate to respective severities of information elements 512 and 514. For example, the patient may be diagnosed with a moderate case of asthma while the patient may suffer from a severe case of eczema. In this example, asthma may be colored yellow (or any other color, shape, graphic, and/or visual indicator to indicate a level of severity) while eczema is colored red (or any other color, shape, graphic, and/or visual indicator to indicate a level of severity). These and/or any techniques described herein may be combined to vary the display of information elements, thereby enriching the display with information that is readily ascertainable by the doctor.

Figure 5B:
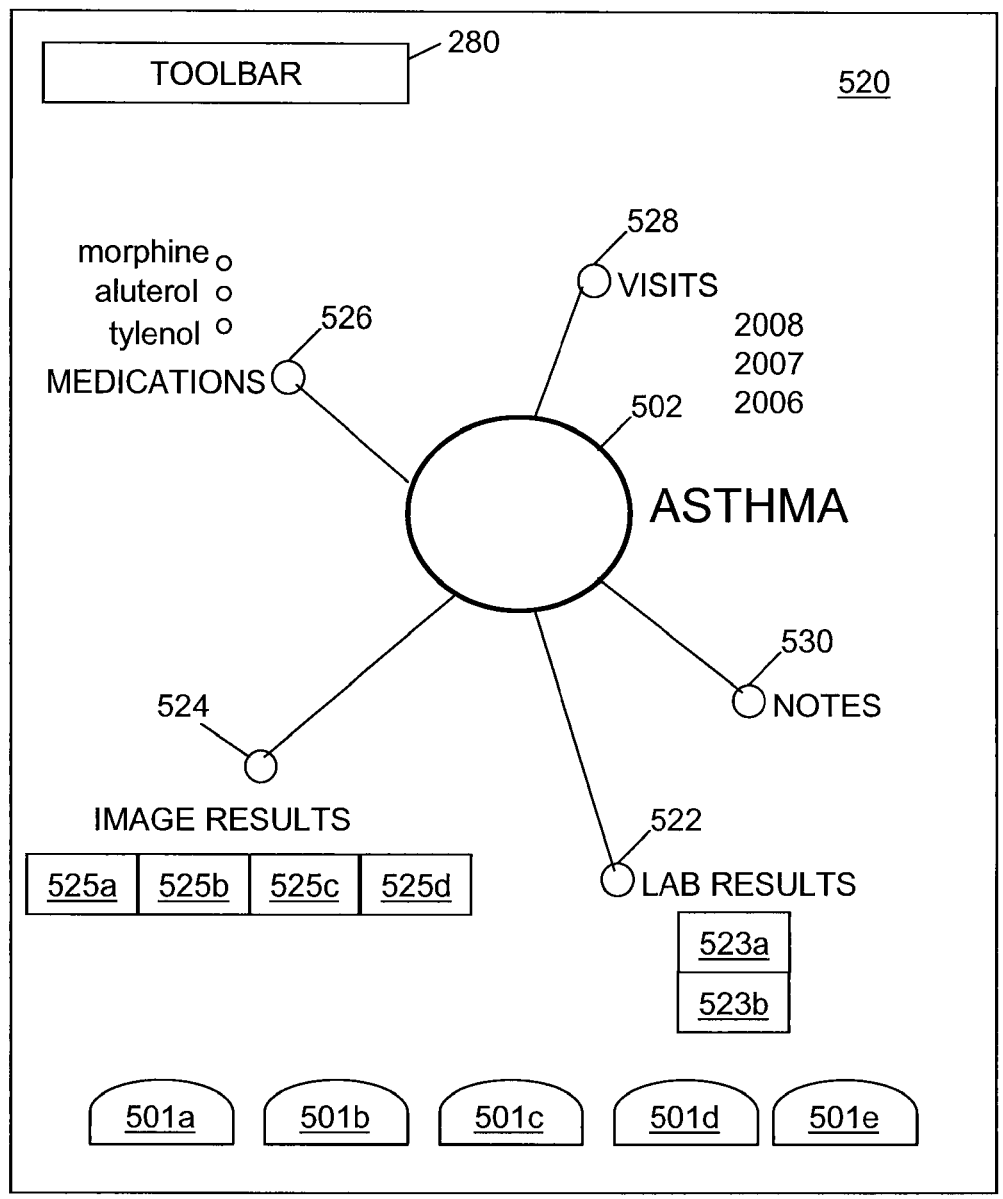
FIG. 5b illustrates a screenshot of an exemplary multi-dimensional cloud view display for an information element, according to an aspect of the invention.

FIG. 5b illustrates a screenshot of an exemplary multi-dimensional contextual view 520, according to an aspect of the invention. FIG. 5b illustrates an exemplary detailed view of information element 502 (which represents asthma) when a user clicks or otherwise selects information element 502 illustrated in FIG. 5a. The multi-dimensional cloud view 520 may display information element 502 at a focal point in the display, around which various dimensions 522, 524, 526, and 528 may be displayed. Alternatively or additionally, multi-dimensional cloud view 520 may display notes 530 that maintains doctor's annotations regarding the particular patient and/or information element 502. In this manner, information relevant to information element 502 may be viewed across multiple dimensions. For example, dimension 522 may include lab results 523a and 523b associated with the patient's asthma condition. Dimension 524 may include imaging results 525 *a, b, c,* and *d,* which may be images (e.g., chest X-rays) taken in response to the patient's asthma condition. Dimension 526 may include medications used to treat the patient's asthma. Dimension 528 may include grouped visitations by year, during which the patient presented symptoms of asthma. Thus, multi-dimensional cloud view 520 may display information element 502 across multiple dimensions.

Figure 5C:
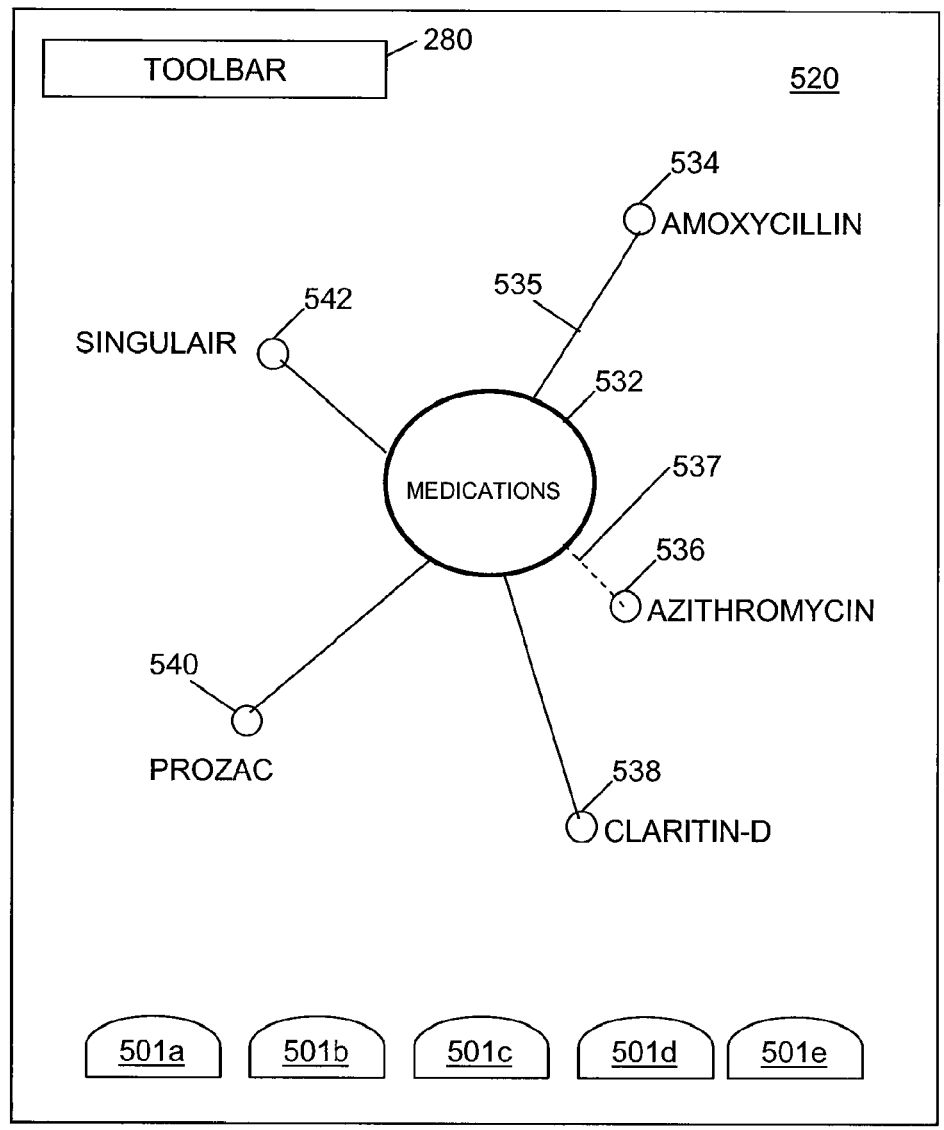
FIG. 5c illustrates a screenshot of an exemplary Medications cloud view display according, to an aspect of the invention.

FIG. 5c illustrates a screenshot of an exemplary Medications cloud view 530 for displaying the Medications dimension of a patient's health record, according to an aspect of the invention. Information elements 534, 536, 538, 540, and 542 may represent drugs in the Medications dimension 532 of the patient and may be graphically depicted and/or spatially arranged about a focal point based on their properties. Information elements 534, 536, 538, 540, and 542 may be depicted as circles that are colored and/or blinking based on their properties. A drug to which the patient is allergic, for example, may be displayed as a blinking red circle while a drug that was stopped due to adverse side effects may be displayed as a blue circle. Other visual indications may be used.

As discussed above, information elements 534, 536, 538, 540, and 542 may be spatially arranged based on their properties. In particular, information element 534 may represent a drug being taken for 10 weeks by the patient while information element 536 may represent a drug being taken by the patient for two weeks. Accordingly, the distance from the focal point "Medications" to the information element 534 may be larger than the distance for information element 536. According to an aspect of the invention, the distance to the focal point may be displayed as a line that is drawn according to properties of the drug. For example, a solid line 535 may indicate that the drug represented by information element 522 is regularly taken by the patient while a dashed line 537 may indicate that the drug represented by information element 524 is taken by the patient as needed. In this manner, the doctor is given a snapshot display of important medications in the medical record of the patient.

Figure 5D:
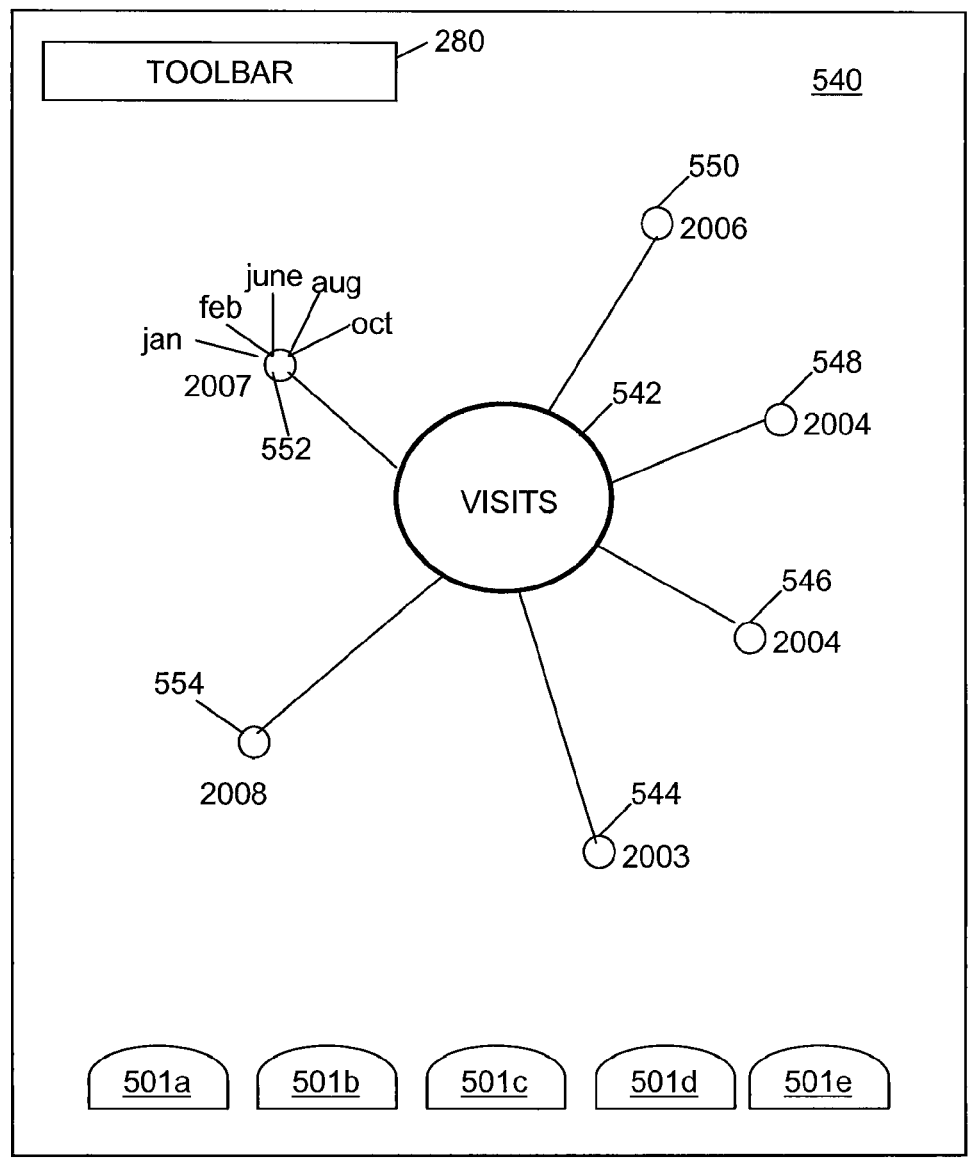
FIG. 5d illustrates a screenshot of an exemplary Office Visits cloud view display, according to an aspect of the invention.

FIG. 5d illustrates a block diagram of a screenshot of an exemplary Office Visits cloud view 540 display for an Office Visits dimension of a patient, according to an aspect of the invention. As previously noted, visitations may include real or virtual visits. Visitations may be grouped by a time period, such as a year, month, week, and/or other time period. According to an aspect of the invention, the time period group may be displayed as an information element in Office Visits dimension cloud view. For example, information elements 544, 546, 548, 550, 552, 554, and 554 may respectively represent visitations grouped by the years 2003, 2004, 2005, 2006, 2007, and 2008. The size of the information elements 544, 546, 548, 550, 552, 554, and 554 may vary with the number of visitations by the patient during the respective year. Alternatively or additionally, information elements representing the year group, for example, may be colored differently based on information element properties for the year. For example, a circle representing a first year may be colored red to indicate that asthma was predominantly presented by the patient in the first year while a second year may be colored blue to indicate that eczema was predominantly presented by the patient in the second year. Other visual indicators may be used.

The information element may be selectable such that clicking on or otherwise selecting a particular year may cause the cloud view module to display detail, such as months, for the particular year. For example, information element 552 is shown after selection by a doctor to view details for visitations during the year 2007. Clicking on (or otherwise selecting) a particular month may cause days in the selected month to appear and selecting a particular day, for example, may cause the office visits module to display information related to a visitation that occurred on the particular day. By viewing a particular day, information across multiple dimensions of the patient's medical record associated with the selected office visit may be displayed. For example, medications prescribed during the selected visit with the doctor, conditions presented during the visit with the doctor, lab results discussed during the visit with the doctor, and/or other multi-dimensional information related to the selected visit with the doctor may be presented.

According to an aspect of the invention, the cloud view module 146 may cause the display to zoom in and out. When zooming out, for example, more information elements may be displayed. In the context of the Office Visits dimension, zooming out may display an increasing number of years of visitations for the patient. In this manner, the doctor may use the Office Visits dimension cloud view to graphically view prior visitations across multiple dimensions.

Figure 5E:
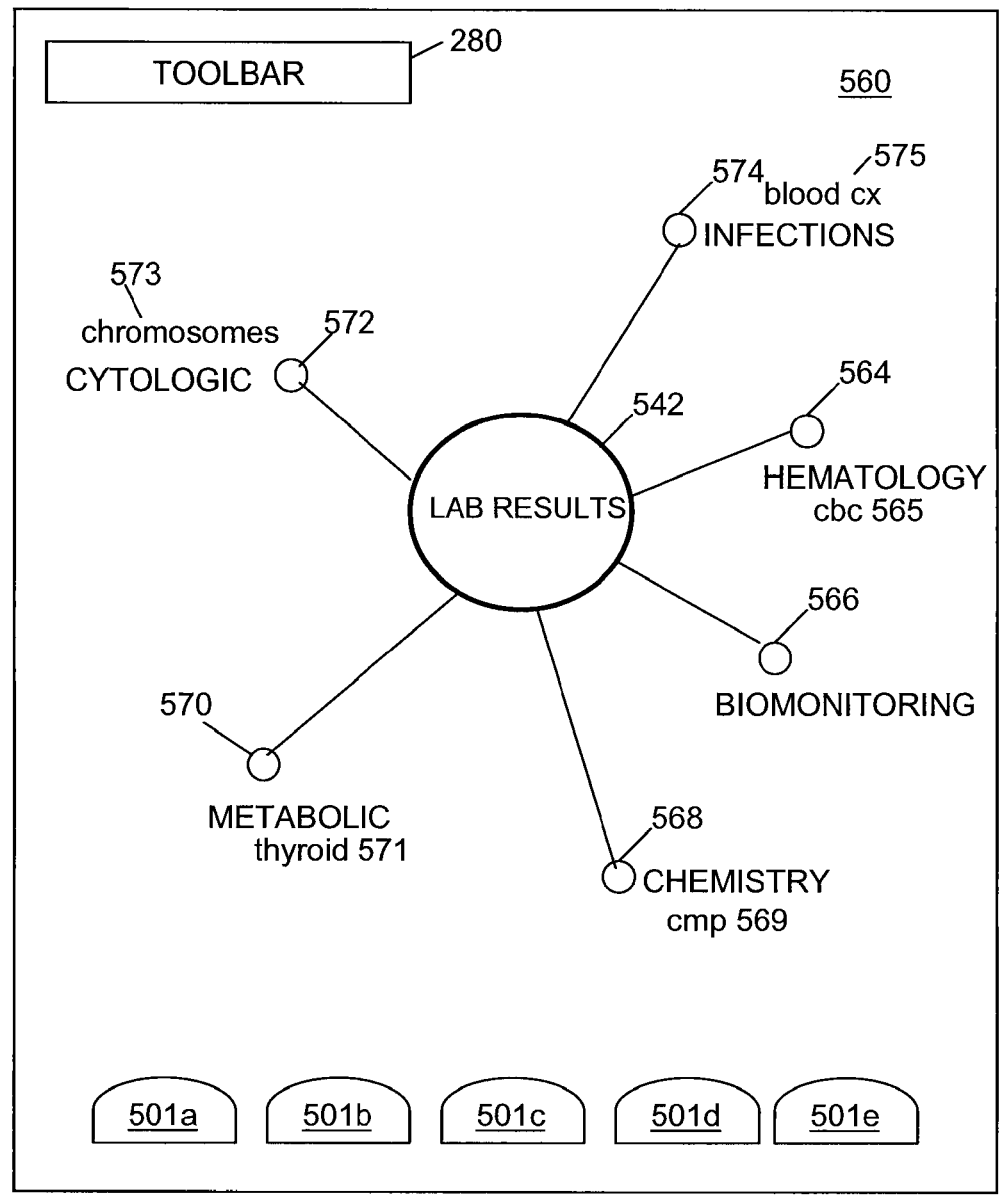
FIG. 5e illustrates a screenshot of an exemplary Lab Results cloud view display, according to an aspect of the invention.

FIG. 5e illustrates a screenshot of an exemplary Lab Results cloud view 560 for displaying the Lab Results dimension 562 of a patient's medical record, according to an aspect of the invention. As discussed above, information elements may represent categories. In the Lab Results dimension 562, for example, information element 564 may represent the category "hematology," which may include information elements 565 related to blood cell test results (e.g., red blood cell count, white blood cell count, etc.). Information element 570 may represent the category "metabolic," which may include information elements 571 related to metabolic activity test results (e.g., thyroid activity). When displaying the Lab Results cloud view, the cloud view module 146 may display "Lab Results" as a focal point 562, around which information element categories 564, 566, 568, 570, 572, and 574 (among other things) are arranged. A distance from an information element category 564, 566, 568, 570, 572, and 574 to the focal point 562 may vary based on the date in which a lab test categorized in the information element category was performed and/or received (e.g., the latest date of a test result in the hematology category). The cloud view module 146 may vary the size of an information element category based on a number of test results included in the information element category. For example, when the medical record of a patient includes more test results for the hematology category than for the metabolic category, information element 564 may be displayed as a larger circle than information element 570 on the Lab Results cloud view. Alternatively or additionally, the cloud view module 146 may vary the color of an information element category based on a number of critical values of information elements within the information element category. For example, the information element 564 may be colored red when five or more lab results in the hematology category are considered abnormal.

According to an aspect of the invention, the doctor may "tag" a particular information element and/or information element category. The cloud view engine may highlight the tagged information element whenever the lab results dimension is viewed. Alternatively or additionally, the tag may facilitate searching for (or otherwise selecting) the tag in order to view tagged content. For example, a doctor may tag a particular test result as "abnormal WBC" such that subsequent searches for the tag reveals patients having an abnormal WBC test result. In this manner, the cloud view module may be used to graphically review various lab results in a patient's medical record, highlighted by category.

Figure 5F:
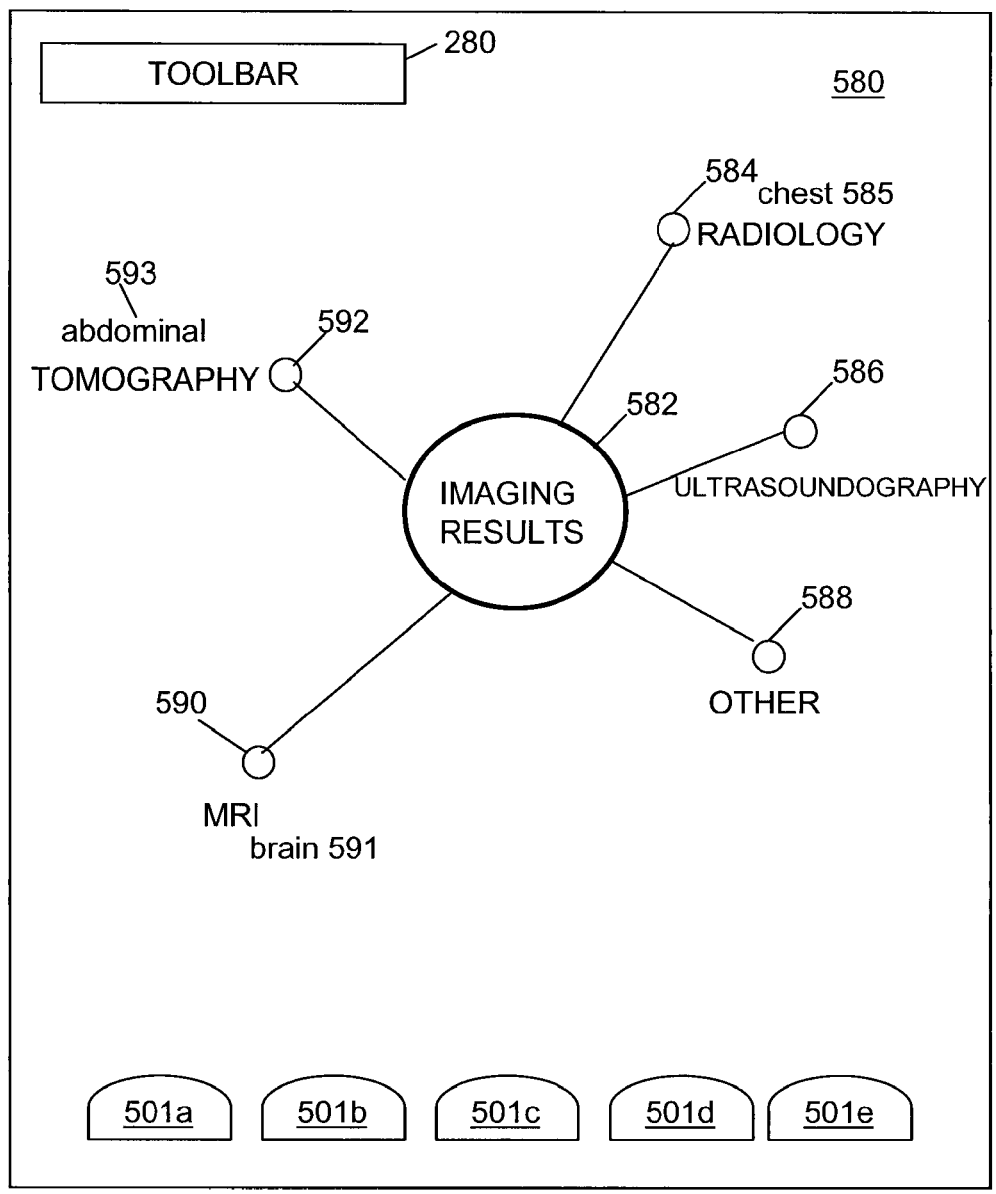
FIG. 5f illustrates a screenshot of an exemplary Imaging Results cloud view display, according to an aspect of the invention.

FIG. 5f illustrates a block diagram of a screenshot of an exemplary Imaging Results cloud view 580 for displaying an Imaging Results dimension 582 of the patient's medical record, according to an aspect of the invention. Like the Lab Results dimension 562, information elements 584, 586, 588, 590, and 592 in the Imaging Results dimension 582 may be categorized and displayed according to a type of imaging result. As such, the doctor may interact with and view Imaging Results dimension 582 in a similar manner.

Figure 6:
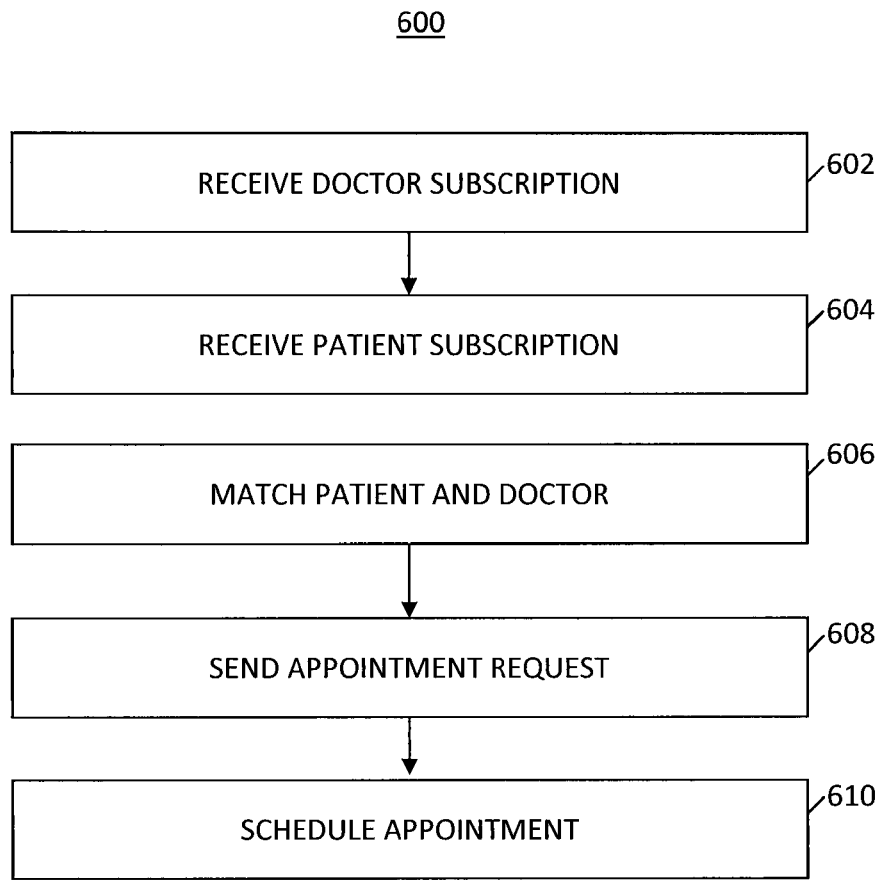
FIG. 6 illustrates a flow diagram of an exemplary method for providing a multi-dimensional contextual platform for facilitating management of a doctor's practice, according to an aspect of the invention.

According to an aspect of the invention, FIG. 6 illustrates a flow diagram of an exemplary process 600 for providing a multi-dimensional contextual platform for facilitating management of a doctor's practice. The various processing operations depicted in the flow diagram of FIG. 6 (and in the other drawing figures) are described in greater detail herein. The described operations for a flow diagram may be accomplished using some or all of the system components described in detail above and, in some implementations, various operations may be performed in different sequences. In other implementations, additional operations may be performed along with some or all of the operations shown in the depicted flow diagrams. In yet other implementations, one or more operations may be performed simultaneously. Accordingly, the operations as illustrated (and described in greater detail below) are exemplary in nature and, as such, should not be viewed as limiting.

In one implementation, a doctor may subscribe to the service in an operation 602. Subscription by the doctor may include various fees such as subscription fees, licensing fees, and/or other fees. Upon subscription, the doctor may register and create doctor profile information. Doctor profile information may include, among other things, education history, background, specialty, personal information, office hours and location, an avatar, and/or other information related to the doctor. In an operation 604, a patient seeking to find one or more doctors may subscribe. Upon subscription, the patient may register and create patient profile information. Patient subscription may solicit various fees from a patient such as subscription fees, usage fees, and/or other fees. Patient profile information may include, among other things, prior and/or current medical conditions, personal information, home address, doctor preferences, specialties needed, an avatar for the patient, and/or other patient profile information. In an operation 606, the subscribed patient may find or otherwise identify a subscribed doctor. In an operation 608, the subscribed patient may send the subscribed doctor an appointment request. In an operation 610, the patient and the doctor may schedule an appointment and the patient may be billed by the doctor for visitations.

Figure 7:
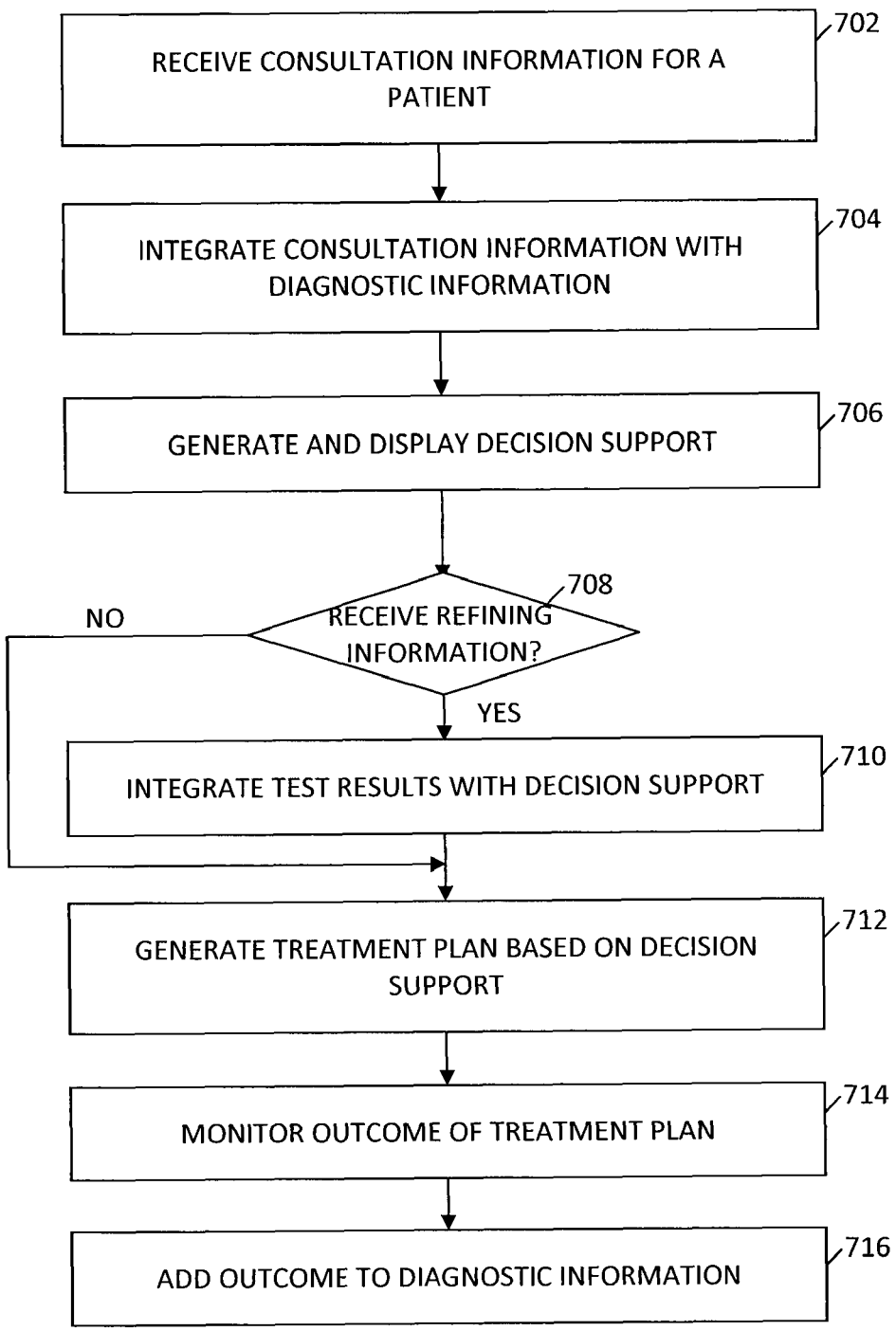
FIG. 7 illustrates a flow diagram of an exemplary method for providing adaptive analysis, according to an aspect of the invention.

According to an aspect of the invention, FIG. 7 illustrates a flow diagram of an exemplary process 700 for providing diagnostic decision suggestions. In one implementation, consultation information may be received in an operation 702. The consultation information may include information from a visitation with the doctor, patient symptoms, or other information related to the patient. In an operation 704, consultation information may be integrated with diagnostic information, which may include, among other things, clinical history, prior doctor examinations of the patient, medications, test results, and prior patient outcomes. The diagnostic information may originate from the patient's health record and/or third party medical repositories that include information from various patients. Integrating consultation information with diagnostic information may include correlating data from the consultation information and the diagnostic information. For example, patient symptoms derived from the consultation information may be correlated with known symptoms associated with various disease states from the diagnostic information.

Based on the integration, decision support information may be generated and displayed in an operation 706. Decision support information may include contextual information providing information to support decision-making (such as suggest to run one or more lab, imaging, or otherwise further diagnostic tests to refine diagnosis and/or suggest potential diagnoses). For example, consultation information for a patient may include information that the patient has presented shortness of breath that suggest that the patient suffers from asthma. These symptoms may be correlated with data from the diagnostic information that indicates shortness of breath is a symptom of asthma. The diagnostic information may include other information that may be helpful to determine that the patient suffers from asthma such as, for example, results from imaging the patient's chest and peak flow readings. Accordingly, the decision support information may include contextual information that suggests taking an image of the patient's chest and obtaining peak flow numbers for the patient.

If in an operation 708 no refining information is received in operation 708, then processing may proceed to operation 712 where a treatment plan may be generated. If in an operation 708, refining information is received (such as, for example, a doctor inputting additional information related to results of the chest imaging and peak flow numbers of the preceding example), processing may proceed to an operation 710, where the refining information may be integrated with the consultation information and the diagnostic information and processing may proceed to operation 712. For example, the chest imaging results and peak flow numbers may be integrated to give a more complete diagnosis in the decision support information. The treatment plan may include one or more treatments directed to treat the patient according to one or more of the potential diagnoses of the decision support information. The treatments may include suggested drug therapy, surgical procedure, and/or other treatment options. In an operation 714, the patient outcome may be monitored by receiving updates to the patient's health condition. For example, the patient outcome may include an indication from the doctor that the patient has responded well to a particular drug therapy that addresses asthma. In an operation 716, the patient outcome may be added to the diagnostic information for the patient to adaptively improve future analyses. For example, other patients with peak flow numbers may respond similarly well to the drug therapy. Alternatively or additionally, the current patient's treatment plan may be modified according to the monitored patient outcome. For example, if the patient did not respond well to the particular drug therapy, a new treatment plan may be adaptively regenerated, taking into account the failed drug therapy (and as such, suggest a new drug therapy or otherwise different course of action).

Figure 8:
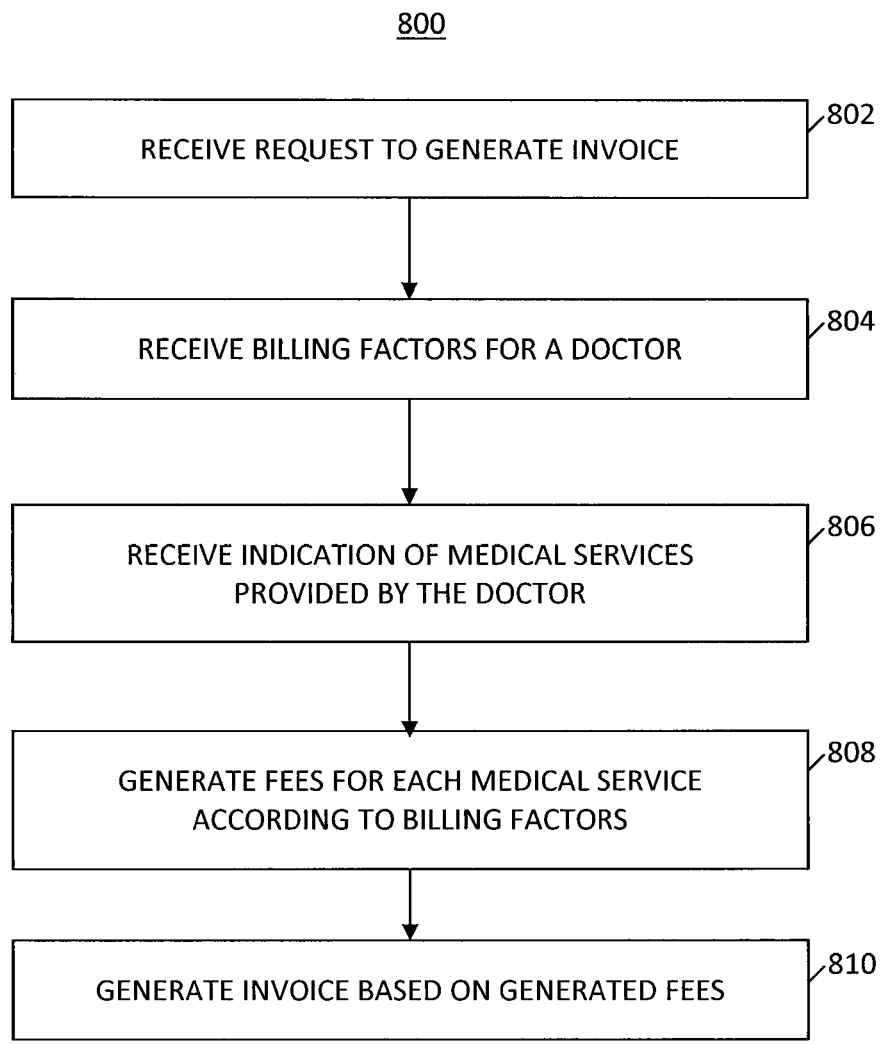
FIG. 8 illustrates a flow diagram of an exemplary method for automatically generating an invoice based on doctor billing factors, according to an aspect of the invention.

According to an aspect of the invention, FIG. 8 illustrates a flow diagram of an exemplary process 800 for automatically generating an invoice based on doctor billing factors. In one implementation, a request to generate an invoice may be received in an operation 802. In an operation 804, one or more billing factors for the doctor may be received. Billing factors may include factors that affect fees and may include, for example, the medical service performed, a method of interaction between the doctor and the patient when the doctor performs the medical service, a fee rate (such as an hourly fee), a fixed fee (such as predefined fees regardless of time), and/or other billing factors. In an operation 806, information indicating medical services performed by the doctor on the patient, and/or methods by which the doctor interacted with the patient may be received. In other words, services by which a fee is to be generated may be received. For each medical service and/or method by which the doctor interacted with the patient, a fee may be determined in an operation 808. In this manner, the doctor may charge different fees according to billing factors such as, for example, the medical service that was performed, the method by which the doctor interacted with the patient when performing the medical service, and/or according to other billing factors. In an operation 810, an invoice may be automatically generated based on the determined fees.

The multi-dimensional contextual platform 120 may comprise an Internet web site, an intranet site, or other application hosted, for example, on one or more servers. According to an aspect of the invention, the multi-dimensional contextual platform 120 may be accessible over a network 108, via any wired or wireless communications link, using one or more user terminals (120). Network 108 may include any one or more of, for instance, the Internet, an intranet, a PAN (Personal Area Network), a LAN (Local Area Network), a WAN (Wide Area Network), a SAN (Storage Area Network), a MAN (Metropolitan Area Network), or other network. Examples of terminal 120 may include any one or more of, for instance, a personal computer, portable computer, personal digital assistant (PDA), workstation, web-enabled mobile phone, WAP device, web-to-voice device, or other device. Those having skill in the art will appreciate that the invention described herein may work with various system configurations.

In addition, implementations of the invention may be made in hardware, firmware, software, or any suitable combination thereof. Aspects of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable storage medium may include read only memory, random access memory, magnetic disk storage media, optical storage media, flash memory devices, and others, and a machine-readable transmission media may include forms of propagated signals, such as carrier waves, infrared signals, digital signals, and others. Further, firmware, software, routines, or instructions may be described herein in terms of specific exemplary aspects and implementations of the invention, and performing certain actions. However, it will be apparent that such descriptions are merely for convenience and that such actions in fact result from computing devices, processors, controllers, or other devices executing the firmware, software, routines, or instructions.

Aspects and implementations described herein as including a particular feature, structure, or characteristic, but every aspect or implementation may not necessarily include the particular feature, structure, or characteristic. Further, when a particular feature, structure, or characteristic is described in connection with an aspect or implementation, it will be understood that such feature, structure, or characteristic may be included in connection with other aspects or implementations, whether or not explicitly described. Thus, various changes and modifications may be made to the provided description without departing from the scope or spirit of the invention. As such, the specification and drawings should be regarded as exemplary only, and the scope of the invention to be determined solely by the appended claims.

What is claimed is:

1. A medical record display device for displaying information from at least one medical record of a patient, the medical record display device comprising:

one or more processors programmed by computer program instructions to:

obtain the at least one medical record of a patient, wherein the at least one medical record comprises a plurality of dimensions that each describe an aspect of a health of the patient, and wherein at least one dimension comprises a first information element and a second information element that each represent medical information related to the at least one dimension, wherein the plurality of dimensions comprise a medical conditions dimension that describes medical conditions of the patient, a visits dimension that describes interactions with the patient, a medications dimension that describes medications taken by the patient, a lab results dimension that describes laboratory results of the patient, or an imaging results dimension that describes imaging results of the patient;

receive a selection to display the at least one dimension;

determine a first location of the first information element and a second location of the second information element to be displayed on a user interface;

determine a first level of importance of the first information element relative to the second information element and a second level of importance of the second information element relative to the first information element, wherein the first level of importance of the first information element is determined based on a first number of interactions between a doctor and the patient related to the first information element compared to a second number of interactions between the doctor and the patient related to the second information element, wherein the first information element is determined to be relatively more important than the second information element when the first number is greater than the second number; and generate a display comprising the first information element based on the first level of importance and the second information element based on the second level of importance, wherein the first information element is displayed as a first geometric shape and the second information element is displayed as a second geometric shape, and wherein the first geometric shape is displayed as a larger geometric shape relative to the second geometric shape when the first information element is determined to be more important than the second information element.

2. The medical record display device of claim 1, wherein the one or more processors are further programmed to:

determine a first location of the first information element based on a first time the first information element appeared in the at least one medical record of the patient.

3. The medical record display device of claim 1, wherein a first level of importance of the first information element is determined based on a first level of severity of the first information element relative to a second level of severity of the second information element, wherein the first information element is relatively more important than the second information element when the first level of severity is greater than the second level of severity.

4. The medical record display device of claim 1, wherein the first information element is displayed as a first color and the second information element is displayed as a second color, and wherein the first color is displayed as a different color relative to the second color when the first information element is determined to be more important than the second information element.

5. A medical record display device for displaying at least one medical record of a patient, the medical record display device comprising:
one or more processors programmed by computer program instructions to:
receive the at least one medical record of a patient, wherein the at least one medical record comprises a plurality of dimensions that each describe an aspect of a health of the patient, and wherein each dimension comprises at least one information element that represents medical information related to the respective dimension, wherein the plurality of dimensions comprise a medical conditions dimension that describes medical conditions of the patient, a visits dimension that describes interactions with the patient, a medications dimension that describes medications taken by the patient, a lab results dimension that describes laboratory results of the patient, or an imaging results dimension that describes imaging results of the patient;
receive a selection to display a dimension;
determine a first location of a dimension indicator that indicates the selected dimension and a second location of the at least one information element to be displayed, wherein the dimension indicator is displayed as a focal point about which the at least one information element is disposed;
generate a display comprising the focal point, the at least one information element, and a line that connects the focal point and the at least one information element, wherein the focal point comprises a circular shape, and the at least one information element comprises a plurality of information elements arranged about the circumference of the circular shape, wherein the line is differentially displayed based on one or more properties of the at least one information element;
receive a selection to display the at least one dimension;
determine a first location of the first information element and a second location of the second information element to be displayed on a user interface; and
determine a first level of importance of the first information element relative to the second information element and a second level of importance of the second information element relative to the first information element, wherein the first level of importance of the first information element is determined based on a first number of interactions between a doctor and the patient related to the first information element compared to a second number of interactions between the doctor and the patient related to the second information element, wherein the first information element is determined to be relatively more important than the second information element when the first number is greater than the second number,
wherein the display comprises the first information element based on the first level of importance and the second information element based on the second level of importance.

6. The medical record display device of claim 5, wherein the at least one information element comprises one or more properties that describe the at least one information element, and wherein the one or more processors of the cloud view module are further configured to display the at least one information element at a distance from the dimension indicator based on the one or more properties.

7. The medical record display device of claim 5, wherein the at least one information element relates to a medication being taken by the patient and the one or more properties comprises a length of time the medication has been taken by the patient, and wherein the distance from the dimension indicator is determined based on the length of time.

8. A computer-implemented method for displaying information from at least one medical record of a patient, the method comprising:
obtaining, by one or more processors programmed by computer program instructions, the at least one medical record of a patient, wherein the at least one medical record comprises a plurality of dimensions that each describe an aspect of a health of the patient, and wherein at least one dimension comprises a first information element and a second information element that each represent medical information related to the at least one dimension, wherein the plurality of dimensions comprise a medical conditions dimension that describes medical conditions of the patient, a visits dimension that describes interactions with the patient, a medications dimension that describes medications taken by the patient, a lab results dimension that describes laboratory results of the patient, or an imaging results dimension that describes imaging results of the patient;
receiving, by the one or more processors, a selection to display the at least one dimension;
determining, by the one or more processors, a first location of the first information element and a second location of the second information element to be displayed on a user interface;
determining, by the one or more processors, a first level of importance of the first information element relative to the second information element and a second level of importance of the second information element relative to the first information element, wherein the first level of importance of the first information element is determined based on a first number of interactions between a doctor and the patient related to the first information element compared to a second number of interactions between the doctor and the patient related to the second information element, wherein the first information element is determined to be relatively more important than the second information element when the first number is greater than the second number; and
generating, by the one or more processors, a display comprising the first information element based on the first level of importance and the second information element based on the second level of importance, wherein the first information element is displayed as a first geometric shape and the second information element is displayed as a second geometric shape, and wherein the first geometric shape is displayed as a larger geometric shape relative to the second geometric shape when the first information element is determined to be more important than the second information element.

9. The computer-implemented method of claim 8, the method further comprising:
determining, by the one or more processors, a first location of the first information element based on a first time the first information element appeared in the at least one medical record of the patient.

10. The computer-implemented method of claim 8, wherein a first level of importance of the first information element is determined based on a first level of severity of the first information element relative to a second level of severity of the second information element, wherein the first information element is relatively more important than the second information element when the first level of severity is greater than the second level of severity.

11. The computer-implemented method of claim 8, wherein the first information element is displayed as a first color and the second information element is displayed as a second color, and wherein the first color is displayed as a different color relative to the second color when the first information element is determined to be more important than the second information element.

12. A computer-implemented method for displaying at least one medical record of a patient, the method comprising:

receiving, by one or more processors programmed by computer program instructions, the at least one medical record of a patient, wherein the at least one medical record comprises a plurality of dimensions that each describe an aspect of a health of the patient, and wherein each dimension comprises at least one information element that represents medical information related to the respective dimension, wherein the plurality of dimensions comprise a medical conditions dimension that describes medical conditions of the patient, a visits dimension that describes interactions with the patient, a medications dimension that describes medications taken by the patient, a lab results dimension that describes laboratory results of the patient, or an imaging results dimension that describes imaging results of the patient;

receiving, by the one or more processors, a selection to display a dimension;

determining, by the one or more processors, a first location of a dimension indicator that indicates the selected dimension and a second location of the at least one information element to be displayed, wherein the dimension indicator is displayed as a focal point about which the at least one information element is disposed; and generating, by the one or more processors, a display comprising the focal point, the at least one information element, and a line that connects the focal point and the at least one information element, wherein the focal point comprises a circular shape, and the at least one information element comprises a plurality of information elements arranged about the circumference of the circular shape;

differentially displaying, by the one or more processors, the line based on one or more properties of the at least one information element;

receiving, by the one or more processors, a selection to display the at least one dimension;

determining, by the one or more processors, a first location of the first information element and a second location of the second information element to be displayed on a user interface; and determining, by the one or more processors, a first level of importance of the first information element relative to the second information element and a second level of importance of the second information element relative to the first information element, wherein the first level of importance of the first information element is determined based on a first number of interactions between a doctor and the patient related to the first information element compared to a second number of interactions between the doctor and the patient related to the second information element, wherein the first information element is determined to be relatively more important than the second information element when the first number is greater than the second number, wherein the display comprises the first information element based on the first level of importance and the second information element based on the second level of importance.

13. The computer-implemented method of claim 12, wherein the at least one information element comprises one or more properties that describe the at least one information element, and wherein the one or more processors of the cloud view module are further configured to display the at least one information element at a distance from the dimension indicator based on the one or more properties.

14. The computer-implemented method of claim 12, wherein the at least one information element relates to a medication being taken by the patient and the one or more properties comprises a length of time the medication has been taken by the patient, and wherein the distance from the dimension indicator is determined based on the length of time.

* * * * *

UNITED STATES PATENT AND TRADEMARK OFFICE
CERTIFICATE OF CORRECTION

| | |
|---|---|
| PATENT NO. | : 8,620,683 B2 |
| APPLICATION NO. | : 13/251934 |
| DATED | : December 31, 2013 |
| INVENTOR(S) | : Nathanial B. Findlay et al. |

It is certified that error appears in the above-identified patent and that said Letters Patent is hereby corrected as shown below:

On the title page, in Item (75) Inventors, change "Nathaniel B. Findlay" to --Nathanial B. Findlay--.

Signed and Sealed this
Twenty-first Day of April, 2015

Michelle K. Lee
*Director of the United States Patent and Trademark Office*